United States Patent
Plank et al.

(10) Patent No.: US 9,222,863 B2
(45) Date of Patent: Dec. 29, 2015

(54) METHOD FOR DETERMINATION OF DIETARY FIBER CONTENT BY CENTRIFUGATION

(71) Applicant: General Mills, Inc., Minneapolis, MN (US)

(72) Inventors: David W. Plank, Golden Valley, MN (US); Lindsey M. Hirsch, Golden Valley, MN (US)

(73) Assignee: General Mills, Inc., Minneapolis, MN (US)

( * ) Notice: Subject to any disclaimer, the term of this patent is extended or adjusted under 35 U.S.C. 154(b) by 0 days.

(21) Appl. No.: 14/211,050

(22) Filed: Mar. 14, 2014

(65) Prior Publication Data

US 2014/0308692 A1    Oct. 16, 2014

Related U.S. Application Data

(60) Provisional application No. 61/783,059, filed on Mar. 14, 2013.

(51) Int. Cl.

| | |
|---|---|
| *C12Q 1/34* | (2006.01) |
| *G01N 3/16* | (2006.01) |
| *G01N 1/38* | (2006.01) |
| *G01N 1/40* | (2006.01) |
| *G01N 33/02* | (2006.01) |

(52) U.S. Cl.
CPC .................. *G01N 3/165* (2013.01); *G01N 1/38* (2013.01); *G01N 1/4077* (2013.01); *G01N 33/02* (2013.01)

(58) Field of Classification Search
CPC ..................................................... G01N 3/165
See application file for complete search history.

(56) References Cited

PUBLICATIONS

Kurup et al. The American J of Clinical Nutrition, 1984, 40:961-963.*
Frolich et al. Cereal Chem., 1984, 61(4):357-359.*
"AACC International Method 32-07.01: Soluble, Insoluble and Total Dietary Fiber in Foods and Food Products," AACC International Approved Methods of Analysis, 11th Edition, Oct. 16, 1991, 9 pages.
"AOAC Official Method 991.43: Total, Soluble, and Insoluble Dietary Fiber in Foods," AOAC Official Methods of Analysis, Supplement Mar. 1995, Chapter 32. 4 pages.
Caldwell et al., "Development of an Analytical Reference Standard for Total, Insoluble, and Soluble Dietary Fiber," Cereal Foods World, May 1999, vol. 44, No. 5, pp. 360-362.
Lee et al., "Determination of Soluble and Insoluble Dietary Fiber in Psyllium-containing Cereal Products," Journal of the AOAC International, 1995, vol. 78, No. 3, pp. 724-729.
Quemener et al., "Determination of Inulin and Oligofructose in Food Products, and Intergration in the AOAC Method for Measurement of Total Dietary Fibre, " LWT—Food Science and Technology, Apr. 1994, vol. 27, No. 2, pp. 125-132.

* cited by examiner

*Primary Examiner* — Bin Shen
(74) *Attorney, Agent, or Firm* — Fredrikson & Byron, P.A.

(57) ABSTRACT

The amount of dietary fiber in a sample can be quantified by dissoluting the sample to produce a dietary fiber solution and then centrifuging the dietary fiber solution to produce a pellet and a supernatant liquid. After separating the supernatant liquid from the pellet, the pellet can be analyzed to determine a content of non-dietary fiber components in the pellet. The dietary fiber content in the pellet can be determined from the content of the non-dietary fiber components in the pellet. By using centrifugation to help isolate the dietary fiber in the sample, fiber loss may be minimized, leading to a more accurate determination of the content of dietary fiber in the sample.

12 Claims, 5 Drawing Sheets

METHOD FOR DETERMINATION OF DIETARY FIBER CONTENT BY CENTRIFUGATION

This application claims the benefit of U.S. Provisional Patent Application No. 61/783,059, filed Mar. 14, 2013, and entitled "METHOD FOR DETERMINATION OF DIETARY FIBER IN FOODS AND BEVERAGES BY CENTRIFUGATION", the entire contents of which are incorporated herein by reference.

TECHNICAL FIELD

This disclosure relates to techniques for quantifying dietary fiber in samples and, more particularly, to the production and validation of consumable products with controlled amounts of dietary fiber.

BACKGROUND

Dietary fiber is an important nutrient in human and animal nutrition that provides direct physiological benefits to the organism. Among the physiological benefits which dietary fiber has been shown to confer include: laxation; blood glucose attenuation; blood lipid attenuation; satiety; weight-loss; and growth stimulation of beneficial probiotic organisms. Regulatory bodies around the world recognize the beneficial health effects of dietary fiber in human and animal nutrition. As a result, health claims based on the dietary fiber content of food are allowed in most countries around the world.

Food products claiming beneficial dietary fiber content have a competitive advantage in segments of the marketplace. For example, food manufacturers may be able to market their products as healthful and beneficial if the products have appropriate amounts of dietary fiber. This has led many food manufacturers to fortify their food products with various dietary fibers. In many instances, this fortification can add significant cost to the manufacture of the food product. Thus, achieving accurate quantification of all dietary fiber fortified into a food product by analytical methods has significant cost impact for food manufacturers and reduces the need for over-fortification while improving profitability.

For purposes of affirming dietary fiber content for both health claims and nutritional labeling, international regulatory agencies and food manufacturers rely primarily on official methods of the Association of Analytical Chemists (AOAC) International. Among the methods typically used for nutritional labeling are AOAC 985.29; AOAC 991.43; AOAC 991.42; AOAC 993.19; AOAC 2009.01; AOAC 2011.25; and AOAC 2001.03. For all of these official AOAC methods, a glass fritted crucible is used for the isolation and quantification of dietary fiber. During analysis, a sample containing dietary fiber is filtered through the crucible to isolate dietary fiber. The solid material separated from the filtrate is then analyzed using various techniques to quantify the amount of dietary fiber.

Unfortunately, the filtering process is not always efficient and can allow significant amounts of dietary fiber to pass through with the filtrate, resulting in an under-quantification of the true dietary fiber content of the sample tested. For manufacturers adding dietary fiber to a product, the under-quantification of dietary fiber content in a sample can cause a manufacturer to over-fortify their products with fiber during production in an effort to meet a target level of fiber content. If the true dietary fiber content of a sample could be more accurately measured, the manufacturer could more precisely control the amount of dietary fiber added to the product during manufacture.

SUMMARY

In general, this disclosure is directed to dietary fiber-containing products, techniques for measuring the amount dietary fiber in a product, and manufacturing techniques for adjusting the amount of dietary fiber added to a product based on the measured dietary fiber content of a sample. In some examples, the dietary fiber content of a sample is determined by dissoluting a dietary fiber-containing sample to produce a dietary fiber solution. The dissolution process can help liberate dietary fiber from other components binding the dietary fiber, such as various fats, proteins, and like. After preparing the dietary fiber solution, the solution is centrifuged to produce a pellet and a supernatant liquid. The pellet is the agglomerated solid from the solution. The pellet contains dietary fiber for further quantification and, in different examples, the supernatant liquid may or may not also contain dietary fiber. In either case, the supernatant liquid can be separated from the pellet and the pellet then analyzed to quantify the amount of dietary fiber in the pellet. For example, different portions of the pellet may be separately analyzed to quantify non-dietary fiber components in the pellet. As one example, one portion of the pellet may be analyzed to quantify the protein content in the pellet and a second portion of the pellet may be analyzed to quantify the ash content in the pellet. The dietary fiber content in the pellet can be determined by subtracting the weight of the non-dietary fiber components from the initial weight of the pellet. In such applications, the remaining weight of the pellet after subtracting off the weight of the non-dietary fiber components can be classified as being the weight of the dietary fiber in the pellet. In this way, the dietary fiber content of a sample can be determined.

The measured dietary fiber content of a sample may be accurately determined by centrifuging the sample at one or more processing steps to isolate the dietary fiber for quantification. In centrifugation, centrifugal force is used to separate molecules according to their size, shape, density, and viscosity. For example, a solution containing solid dietary fiber and liquid dissoluted non-dietary fiber components can be centrifuged to separate the larger, higher molecular weight components from the smaller, lower molecular weight components or soluble components. The resulting supernatant liquid can then be extracted from the resulting solid pellet to provide a solid rich in dietary fiber for further analysis.

In contrast to a filtration technique where a dietary fiber solution is passed through a filter to separate solid dietary fiber from liquid dissoluted non-dietary fiber components, centrifugation may provide a more accurate separation between the fiber and non-fiber components. For example, during filtration, solid dietary fiber may become entrained with the liquid dissoluted non-dietary fiber components, causing some amount of the dietary fiber to pass through the filter into the filtrate. This can occur when the filter is too larger for the fiber particle size distribution, allowing small size particles to pass into the filtrate. This dietary fiber passing into the filtrate is lost from the remainder of the solid dietary fiber separated by filtration, resulting in under-quantification of the dietary fiber content of the sample. Centrifugation can help avoid dietary fiber loss to a filtrate by mechanically separating the solid dietary fiber from the liquid dissoluted non-dietary fiber components through the application of centrifugal force, e.g., within a centrifugation tube. Thus, centrifugation can increase the amount of dietary fiber isolated by reduction of loss relative to fiber isolated by filtration. In applications where a manufacturer is adding dietary fiber to a product in an amount effective to meet a minimum threshold (e.g., 5 weight percent, 10 weight percent), a small under-quantification of fiber content at the lab scale can necessitate large excess volumes of fiber being added during production of the product to achieve the stated threshold. Accordingly, with a better understanding of the true dietary fiber content of the product, the manufacturer can more accurately control the amount of fiber added during production.

Although the specific technique can vary, in some examples, various steps may be taken to help minimize dietary fiber loss during quantification of dietary fiber content in a sample. In one example, a temperature gradient is established between a centrifuge container holding a dietary fiber solution and the centrifuge itself during centrifugation. For example, the centrifuge container holding the solution may be heated prior to inserting the container in the centrifuge which, itself, is comparatively cold. The temperature differential may lead to better separation of thermally sensitive components, such as fat and protein, from the dietary fiber and/or better layering between the components during centrifugation. As another example, upon centrifuging a dietary fiber solution to produce a dietary fiber-containing pellet and a supernatant liquid, the supernatant liquid may be aspirated out of the centrifuge container while leaving the pellet in the container for further processing. Dietary fiber loss associated with mass transfer from one container to another container can be minimized or eliminated by following such a technique.

In one example, a method for determining fiber content is described that includes dissoluting a dietary fiber-containing sample and thereby producing a dietary fiber solution. The method also includes centrifuging the dietary fiber solution so as to produce a pellet and a supernatant liquid and separating the supernatant liquid from the pellet. The method further includes analyzing at least a portion of the pellet to determine a content of non-dietary fiber components in the pellet and determining therefrom a dietary fiber content in the pellet.

In another example, a method is described that includes enzymatically digesting a dietary fiber-containing sample and thereby producing a dietary fiber solution. The method also includes centrifuging the dietary fiber solution so as to produce a pellet and a supernatant liquid and extracting the supernatant liquid from the pellet. The method further includes combining the pellet with a solvent such that fat in the pellet dissolves in the solvent and thereby produces a dissolved fat solution and further centrifuging the dissolved fat solution so as to produce a second pellet and a second supernatant liquid. The method also includes drying the second pellet to produce a dried sample and analyzing at least a portion of the dried sample to determine a content of non-dietary fiber components in the dried sample and determining therefrom a dietary fiber content in the dried sample.

In various examples, the disclosed techniques may involve isolating fiber components from dissolved non-fiber components by centrifugation instead of the crucible filtering. The use of a high speed centrifuge can efficiently separate dietary fiber components and isolate the components with good yield and without the use of celite. The example techniques may also involve tempering a dietary fiber-containing solution with a temperature regime such that the solution is raised above the temperature by which the sample will be centrifuged for a period of time. Further, during centrifuging, a reduced oxygen environment can be established within the centrifuge, for example by creating an inert gas blanket in the centrifuge, to mitigate the risk of fire and explosion from centrifugation of flammable and explosive solutions.

Independent of the specific techniques used to help isolate dietary fiber-rich solid from a remainder of a sample, the resultant solid can be dried and the dietary fiber content of the solid quantified. In some examples, the solid is freeze dried and then homogenized by mechanical blending of the dried product. This can allow the dried solid to be separated into multiple different portions for independent analyses of different non-dietary fiber components rather than requiring the overall technique to be repeatedly performed to generate each of the different portions needed for analysis.

The details of one or more examples are set forth in the accompanying drawings and the description below. Other features, objects, and advantages will be apparent from the description and drawings, and from the claims.

DETAILED DESCRIPTION

Figure 1:
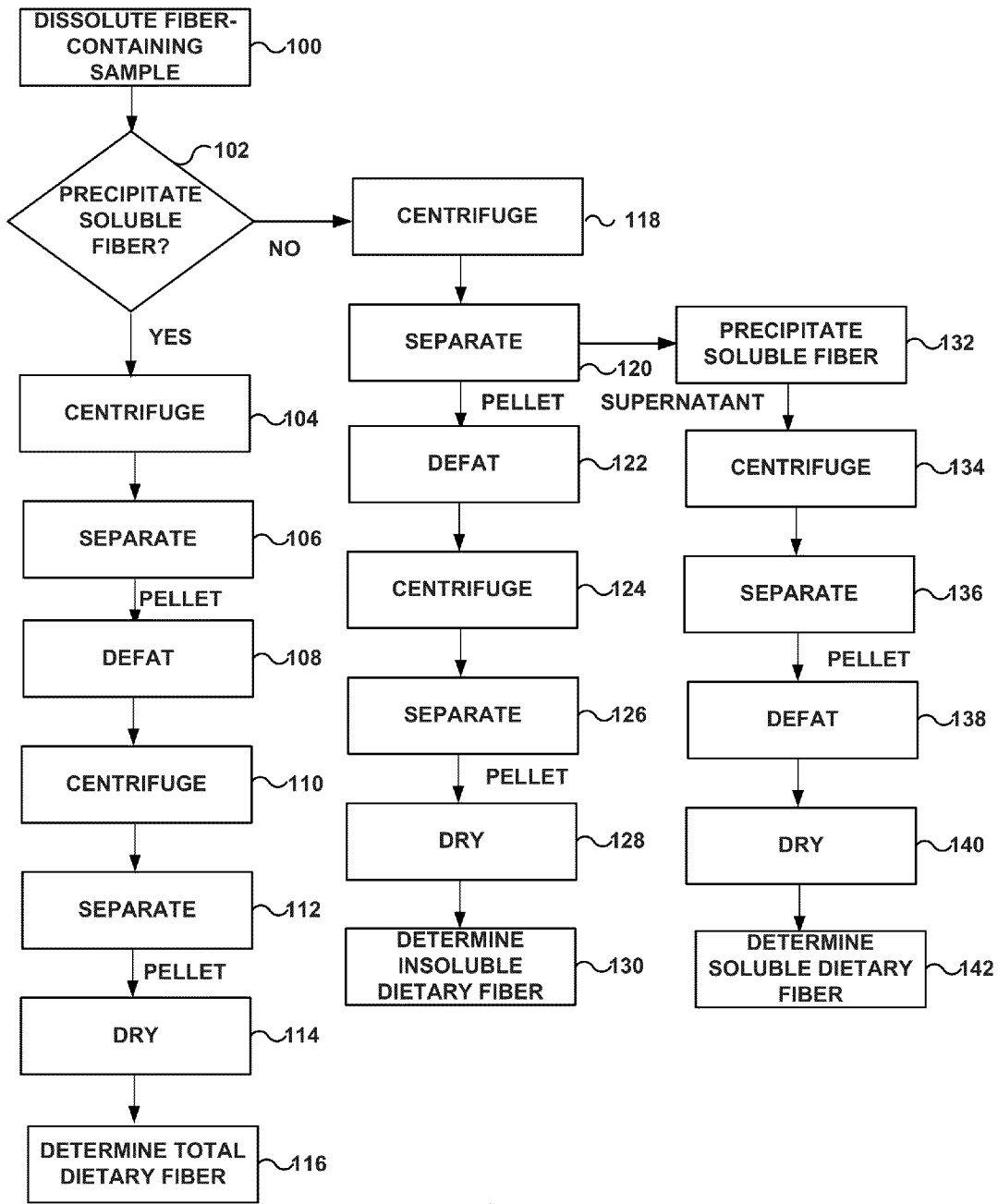
FIG. 1 is a flow diagram illustrating an example process for determining the fiber content of a product.

In general, this disclosure relates to dietary fiber-containing products and the quantification of dietary fiber content in such products. The term dietary fiber generally refers to the coarse, indigestible plant matter, composed primarily of polysaccharides such as cellulose, that when eaten by humans stimulates intestinal peristalsis. For example, dietary fiber can include cell wall materials such as cellulose, hemicelluloses, lignin, and pectins, along with gums and mucilages that are not digested by the body. According to the American Association of Cereal Chemistry (2000): "Dietary fiber is defined as the edible parts of plants or analogous carbohydrates that are resistant to digestion and absorption in the human small intestine with complete or partial fermentation in the large intestine. Dietary fiber includes polysaccharides, oligosaccharides, lignin, and associated plant substances. Dietary fiber promotes beneficial physiological effects including laxation, and/or blood cholesterol attenuation, and/or blood glucose attenuation." Sources of dietary fiber suitable for use in products and quantification in accordance with the disclosure include, but are not limited to, cereal brans, barley, psyllium, legumes, insulin, fructo-oligosaccharides, polydextrose, vegetable sources, fruit sources, grain sources, nuts, and flax seeds.

A wide variety of different products may contain dietary fiber that is desirably quantified. Example products include consumable foods, beverages, and/or nutritional supplements. In some examples, a consumable product containing dietary fiber desirably quantified is a consumable product that is intended for mammalian consumption, such as by humans and/or animals (e.g., cats, dogs, horses, cows). Specific examples of products that may include dietary fiber include animal feed, vitamins, cereal, granola bars, bakery items (e.g., bread, cookies, brownies, muffins), sports energy drinks, milk, cottage cheese, etc. The dietary fiber present in a product may be naturally occurring due to the addition of dietary fiber-containing ingredients to the product. Additionally or alternatively, the dietary fiber present in a product may be deliberately added by first extracting the dietary fiber from a dietary fiber-containing source and then adding the dietary fiber to the product in an effort to increase the dietary fiber content of the product.

Independent of the source of dietary fiber present in a product, the product may contain any suitable amount of dietary fiber. For example, a product may contain from 0.1 weight percent dietary fiber to 100 weight percent dietary fiber, such as from 2 weight percent dietary fiber to 70 weight percent dietary fiber, or from 10 weight percent dietary fiber to 50 weight percent dietary fiber. The weight percentage of dietary fiber present in a product may be determined in accordance with the techniques of the present disclosure. In some countries, governmental regulatory agencies specify the amount of dietary fiber that must be present in a product before a manufacturer and/or retailer can make advertising claims about the beneficial health effects of a product due to the presence of dietary fiber. In the United States, for instance, the Food and Drug Administration (FDA) currently requires that a product contain from 10 weight percent to 19 weight percent of the recommended daily fiber intake (RDI) before making "good source" advertising statements about the health benefits of the product attributable to the dietary fiber content. Accordingly, in some examples, a product may have at least 10 weight percent dietary fiber as determined in accordance with the techniques of the present disclosure. Such a product may or may not have at least 10 weight percent dietary fiber when determining the fiber content using other techniques, such as AOAC 985.29; AOAC 991.43; AOAC 991.42; AOAC 993.19; AOAC 2009.01; AOAC 2011.25; and/or AOAC 2001.03.

FIG. 1 is a flow diagram illustrating an example process for determining the fiber content of a product. The process starts by obtaining a sample of a product containing dietary fiber (referred to herein as a "dietary fiber-containing sample") and dissoluting the fiber-containing sample (100). The dietary fiber within the dietary fiber-containing sample may be intermixed and/or bound with non-dietary fiber components, such as fat, protein, and/or ash. During dissolution, the non-dietary fiber-containing components in the dietary fiber-containing sample can at least partially, and in some examples fully, disintegrate or decompose to help liberate dietary fiber for further isolation and weighing. In different examples, the fiber-containing sample can be dissoluted chemically, enzymatically, thermally (e.g., with application of heat), and/or mechanically (e.g., by application of a mechanical crushing force). During dissolution, the dietary fiber-containing sample may be mixed with a liquid (e.g., aqueous liquid or organic liquid) either as part of a dissolution chemical or enzymatic additive or as a processing solvent to help breakdown the sample. As a result, upon dissolution of the dietary fiber-containing sample, a dietary fiber solution may be formed that includes dietary fiber and dissoluted non-dietary fiber components. In practice, some of the dietary fiber in the dietary fiber solution may be intermixed with and/or bound with residual non-dietary fiber components, the weight of which can be determined through subsequent analysis.

In one example, a dietary fiber-containing sample is dissoluted chemically by mixing the fiber-containing sample with a chemical such as acidified methanol. The acidified methanol can function to dissolute the fiber-containing sample by solubilizing non-dietary fiber components. In another example, the dietary fiber-containing sample is dissoluted enzymatically by mixing the dietary fiber-containing sample with one or more enzymes. The one or more enzymes can be selected, for example, based on the chemical composition of the dietary fiber-containing sample, to digest the non-dietary fiber components of the sample. For example, the dietary fiber-containing sample may first be mixed with an α-amylase that digests non-dietary fiber polysaccharides. The dietary fiber-containing sample combined with α-amylase may be heated above ambient temperature, such as to a temperature greater than 75 degrees Celsius (e.g., 95 to 100 degrees Celsius) to help gelatinize starch molecules in the sample. After suitably cooling the sample with digested polysaccharides (e.g., to a temperature below 75 degrees Celsius, such as below 60 degrees Celsius), the sample can be mixed with a protease and an amyloglucosidase to digest protein and non-dietary fiber polysaccharides, respectively.

Irrespective of the specific chemical(s) and/or enzyme(s) selected to dissolute a dietary fiber-containing sample, the chemical(s) and/or enzyme(s) may be selected to dissolute substantially all components in the sample other than the dietary fiber. For example, the chemical(s) and/or enzyme(s) may be selected to dissolute substantially all (and, in other examples, all) non-dietary fiber components in the dietary fiber-containing sample. In various applications, the chemical(s) and/or enzyme(s) may dissolute greater than 50 weight percent of all non-dietary fiber components in the dietary fiber-containing sample, such as greater than 80 weight percent, greater than 90 weight percent, or greater than 95 weight percent. Despite dissoluting substantial quantities of the non-dietary fiber components, the chemical(s) and/or enzyme(s) may nevertheless dissolute substantially none (and, in other examples, none) of the dietary fiber present in the sample. For example, the chemical(s) and/or enzyme(s) may dissolute less than 10 weight percent of the dietary fiber present in the dietary fiber-containing sample, such as less than 1 weight percent, or less than 0.1 weight percent.

The example technique of FIG. 1 also includes optionally precipitating water-soluble dietary fiber from the dietary fiber solution generated via dissolution (102). Dietary fiber within a dietary fiber-containing sample may be present as both a water-soluble fraction and a water-insoluble fraction. In applications in which a dietary fiber-containing sample is mixed with water, for example as part of a chemical or enzyme added to the sample during dissolution, the water-soluble fraction may solubilize and enter the aqueous phase while the water-insoluble fraction remains in the solid phase. If it is desired to separately determine the amount of water-soluble dietary fiber and/or water-insoluble dietary fiber present in the sample, the aqueous phase of the dietary fiber solution can be separated from the solid phase without first precipitating the water-soluble dietary fiber faction. Conversely, if it is desired to measure the total dietary fiber content of a sample (without separately quantifying the water-soluble and water-insoluble fractions), the water-soluble dietary fiber can be precipitated out of the aqueous phase and back in to the solid phase.

In one example, water-soluble dietary fiber is precipitated from the dietary fiber solution generated via dissolution (102) by mixing the dietary fiber solution with a precipitating agent, such as an alcohol (e.g., ethanol). Although any suitable alcohol can be used, one suitable alcohol that can be used is anhydrous reagent-grade alcohol composed of 90% ethanol, 5% methanol, 5% isopropanol. The mixture of dietary fiber solution and alcohol may be cooled below ambient temperature, such as a temperature below zero degrees Celsius (e.g., −20 degrees Celsius), for example from one to seventy-two hours, such as approximately three hours, to precipitate substantially all the soluble dietary fiber from the aqueous phase to the solid phase.

When a sample under analysis is processed by precipitating water-soluble dietary fiber from the dietary fiber solution generated via dissolution (102), the resultant solution can be centrifuged to separate the solid dietary fiber from the dissoluted non-dietary fiber components (104). During centrifugation, centrifugal force is used to separate the larger, higher molecular weight components from the smaller, lower molecular weight components or soluble components. The dietary fiber solution with precipitated water-soluble dietary fiber can be placed in a centrifuge bottle that is inserted into a centrifuge. The centrifuge can be operated at a force and for a duration effective to separate the solid components in the solution (including the dietary fiber) into an agglomerated pellet at the bottom of the centrifuge bottle and a supernatant liquid containing dissoluted non-dietary fiber components above the solid pellet. Although the force and duration can vary, for example based on the design of the centrifuge and quantity of solution being centrifuged, in some examples, the dietary fiber solution is centrifuged at a force of at least 5,000 times gravity, such as at least 10,000 times gravity, or at least 12,500 times gravity. For example, the dietary fiber solution may be centrifuged at a force ranging from 10,000 times gravity to 25,000 times gravity, such as from 12,500 times gravity to 15,000 times gravity. The dietary fiber solution may be centrifuged at any of these foregoing forces for a duration of at least 5 minutes, such as at least 15 minutes, at 30 minutes, or at least 1 hour. For example, the dietary fiber solution may be centrifuged for a duration ranging from 5 minutes to 1 hour, such as 15 minutes to 45 minutes. It should be noted that use of lower centrifugal force (times gravity) may be compensated for by increasing centrifugation time.

When the dietary fiber solution intended to be centrifuged contains a flammable component, such as alcohol that may be added to precipitate the water-soluble dietary fiber fraction (102), safety precautions may be taken to mitigate the risk of fire and explosion during centrifugation. This may involve reducing the oxygen content or eliminating oxygen from within the centrifuge to reduce the risk of fire and explosion. The centrifuge can be connected to an inert gas source, such as nitrogen or carbon dioxide, to at least partially displace atmospheric oxygen within the centrifuge with the inert gas. If the centrifuge contains a vacuum pump, a gas line connected to a source of inert gas may be attached to the air inlet side of a solenoid valve that switches between vacuum and air venting for the centrifuge rotor chamber. Once the centrifuge is loaded with the container containing the dietary fiber solution, the inert gas can be introduced in to the rotor chamber until the oxygen level falls below a threshold level, such as 0.1%. The centrifuge can then be operated. After reaching a desired operating rate, the solenoid valve can switch to vacuum, causing the rotor chamber to evacuate and maintain the low oxygen content in the chamber. As the centrifuge begins to break to a stop at the end of centrifugation, the solenoid can switch back, reopening the inert gas line and refilling the rotor chamber with the inert gas. In this manner, a low oxygen atmosphere can be established within the centrifuge during operation to help minimize the likelihood of fire or explosion.

Independent of whether any specific precautions are taken to minimize flammability and explosion risk during operation, in some examples, the technique of FIG. 1 includes establishing a thermal gradient between the dietary fiber solution and the centrifuge prior to centrifuging the dietary fiber solution (104). Without wishing to be bound by any particular theory, it is believed that a thermal gradient between the dietary fiber solution and the centrifuge leads to the formation of a more stable dietary fiber pellet, thereby increasing dietary fiber recovery, as compared to if the dietary fiber solution is substantially temperature equilibrated with the centrifuge. For example, a temperature gradient between the dietary fiber solution and the centrifuge can allow components within the sample such as fat, protein, and/or carbohydrate to coalesce as separate components and form layers within the pellet formed by the centrifugation. A more stable pellet may therefore be formed, assisting the efficiency of the centrifugation process and helping to maximize recovery of dietary fiber in the pellet for subsequent quantification.

In applications in which a thermal gradient is created between the dietary fiber solution and the centrifuge, the dietary fiber solution can be heated or cooled relative to the temperature of the centrifuge and/or the centrifuge itself can be heated or cooled relative to the temperature of the dietary fiber solution. In one example, a centrifuge container containing the dietary fiber solution is heated to a temperature above ambient temperature prior to placing the container in the centrifuge, such as a temperature greater than 25 degrees Celsius, a temperature greater than 40 degrees Celsius, or a temperature greater than 60 degrees Celsius. The container can be heated, for example, by placing the container in a hot water bath or incubator. In such an example, the centrifuge may or may not be cooled relative to ambient temperature to increase the magnitude of the temperature differential between the centrifuge and the dietary fiber solution. For example, the centrifuge may be cooled to a temperature below 30 degrees Celsius, such as a temperature below 20 degrees Celsius, or a temperature below 10 degrees Celsius. The centrifuge may be cooled to any one of these foregoing temperatures prior to placing the container in the centrifuge and may or may not also be continuously cooled during centrifugation to maintain any one of these foregoing temperatures throughout the duration of centrifugation.

By heating and/or cooling the dietary fiber solution relative to the centrifuge, a temperature differential between the solution and centrifuge may be created that is greater than 10 degrees Celsius, such as greater than 25 degrees Celsius, or greater than 40 degrees Celsius. The temperature differential may be substantially maintained throughout the duration of centrifugation or may change during centrifugation. In some examples, the temperature differential between the solution and the centrifuge progressively decreases during the course of centrifugation as the solution temperature converges toward temperature equilibration with the centrifuge temperature.

The example technique of FIG. 1 includes separating the supernatant liquid generated through centrifugation from the pellet generated through centrifugation (106). At this point in the quantification process, the pellet may contain substantially all dietary fiber originally present in the sample along with various impurities, such as undissoluted fat, protein, and ash. The supernatant may contain dissoluted non-dietary fiber components and other water-soluble components, such as low-molecular-weight resistant oligosaccharides (maltodextrins). Any suitable technique can be used to separate the supernatant liquid from the pellet. In one example, the supernatant liquid is decanted from the container containing both the pellet and the supernatant liquid, leaving the pellet in the container for further analysis. In another example, the supernatant liquid is aspirated out of the container, again leaving the pellet in the container for further analysis. Alternatively, both the pellet and the supernatant liquid can be removed from the container during separation of the pellet and liquid. For example, the contents of the centrifuge bottle may be poured on a filter to separate the pellet from the supernatant liquid.

Figure 2:
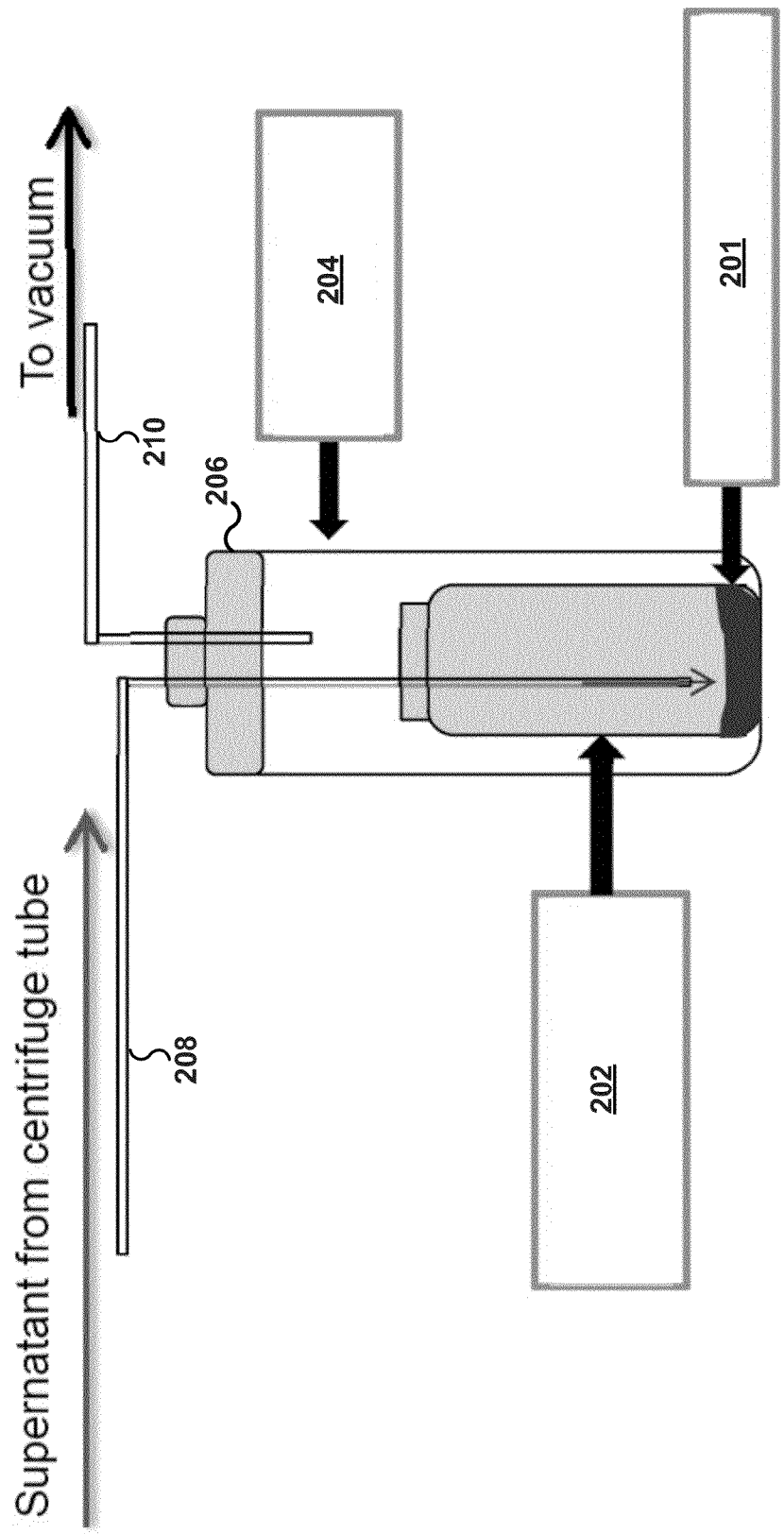
FIG. 2 is illustration of an example apparatus for extracting supernatant liquid from a container containing both supernatant liquid and a pellet via aspiration.

FIG. 2 is illustration of an example apparatus 200 for extracting supernatant liquid 201 from a container containing both the supernatant liquid and the pellet via aspiration. The apparatus includes a supernatant collection container 202 inserted into a pressure container 204 that is sealed with a cap 206 having a port for a supernatant extraction line 208 and a port for a vacuum line 210. In use, the supernatant extraction line 208 is inserted into the centrifuge container containing the supernatant liquid and pellet so the end of the line is positioned in the liquid residing on top of the pellet (not illustrated in FIG. 2). By simultaneously drawing a vacuum through vacuum line 210, a pressure differential is created causing the supernatant liquid 201 to draw up into the supernatant extraction line 208 and away from the pellet. The extracted supernatant liquid 201 is discharged into the supernatant collection container 202. In this manner, the supernatant liquid can be aspirated away from the pellet, helping to minimize physical disturbance of the pellet and attendant dietary fiber loss. In other examples, a pipette may be inserted into the centrifuge container 202 to suction off the supernatant liquid.

With further reference to FIG. 1, the example technique includes optionally de-fatting the dietary fiber-containing pellet separated from the supernatant liquid (108). As discussed above, dietary fiber within the dietary fiber solution generated via dissolution (100) may contain residual components, such as fat, that did not fully separate from the fiber during dissolution. This residual fat can act as a contaminant when attempting to determine the weight of dietary fiber in the sample. De-fatting the dietary fiber-containing pellet (108) can help further isolate the dietary fiber in pellet for quantification. Although useful to remove excess fat from the pellet, in instances in which the original sample contains little or no fat, the de-fatting step (108) may be skipped without materially influencing the results of the dietary fiber quantification. Alternatively, the de-fatting step (108) may be skipped if fat content is also evaluated when determining the weight of non-dietary fiber components, the results of which may form a basis for indirectly determining dietary fiber content (116).

In applications where the dietary fiber-containing pellet is de-fatted (108), the pellet can be combined with a suitable organic solvent to dissolve the fat from the pellet. An example solvent is a 2:1 (volume/volume) acetone/methanol solution, although other organic solvents can be used. In some examples, the dietary fiber-containing pellet is rinsed with the organic solvent, causing any fat contained in the pellet to dissolve and carry away in the solvent. In other examples, the dietary fiber-containing pellet is mechanically mixed with the solvent, causing the pellet to physically break apart and increasing the surface area of the pellet exposed to the solvent. Depending on the characteristics of the pellet, mechanical breakdown of the pellet and intermixing of the broken-down pellet with the solvent can increase fat removal as compared to when the pellet is only rinsed with the solvent.

When a dietary fiber-containing pellet is physically disintegrated and intermixed with organic solvent, the resulting mixture may be a dissolved fat solution containing disintegrated solid dietary fiber (possibly containing residual contaminants such as proteins and/or ash) and dissolved fat entrained with the surrounding organic liquid. To separate the dietary fiber from the surrounding organic liquid, the dissolved fat solution can be centrifuged to produce a de-fatted pellet and a second supernatant liquid formed of the organic liquid containing the dissolved fat (110). When used, centrifugation (110) can be performed using any of the operating parameters, hardware configurations, and techniques discussed above with respect to the first centrifugation (104). After centrifuging the dissolved fat solution to produce the de-fatted pellet and the second supernatant liquid, the de-fatted pellet is separated from the second supernatant liquid (112). Separation can be performed using any of the techniques and equipment configurations discussed above with respect to the first separation (106). For example, the second supernatant liquid may be extracted from the de-fatted pellet via aspiration, e.g., using a hardware apparatus configured as shown in FIG. 2.

The technique of FIG. 1 includes drying the pellet separated from the supernatant liquid to produce a dried solid for further analysis (114). In applications where the pellet is not de-fatted at step (108), the pellet dried for further analysis can be the pellet produced after the first centrifugation (104) following dissolution (100) and precipitation of the water-soluble dietary fiber (102). In other applications where the pellet is de-fatted at step (108), the pellet dried for further analysis can be the de-fatted pellet separated from the second supernatant liquid (110). In still other examples, the technique of FIG. 1 can be performed without drying the pellet prior to determining the total dietary fiber content (116).

A dietary fiber-containing pellet can be dried to produce a dried solid for further analysis using any suitable technique. The dietary fiber-containing pellet can be vacuum dried by creating a sub-ambient pressure around the pellet, causing residual liquid to evaporate from the pellet in the reduced pressure environment. Additional or alternatively, the dietary fiber-containing pellet can be thermally dried. In one example, the dietary fiber-containing pellet is dried in a reduced pressure environment by freeze drying the pellet. Freeze drying enables even moisture removal which results in a more readily homogenous product, whereas thermal drying may cause film formation of the final product leaving it difficult to homogenize. After suitably drying the pellet to produce the dried solid, the dried solid can be analyzed to determine total dietary fiber content, as will be discussed in connection with FIG. 3.

As briefly noted above, dietary fiber within a dietary fiber-containing sample may be present in both a water-soluble fraction and a water-insoluble fraction. If it is desired to determine the amount of water-soluble dietary fiber and/or water-insoluble dietary fiber present in the sample rather than determining total dietary fiber, the aqueous phase of the dietary fiber solution can be separated from the solid phase without first precipitating the water-soluble dietary fiber fraction (102). For example, the dietary fiber solution generated via dissolution (100) may be centrifuged directly (118) without first precipitating the water-soluble dietary fiber out of the aqueous phase and back in to the solid phase. Centrifugation of the dietary fiber solution can yield an agglomerated solid pellet containing the water-insoluble dietary fiber (and substantially no water-soluble dietary fiber) and a supernatant liquid containing the water-soluble dietary fiber (and substantially no water-insoluble dietary fiber). The pellet containing the water-insoluble dietary fiber can then be separated from the supernatant liquid containing the water-soluble dietary fiber (120), for example, to facilitate separate quantification of each dietary fiber fraction.

In such applications, centrifugation (118) of the dietary fiber sample containing unprecipitated water-soluble dietary fiber can be performed using any of the operating parameters, hardware configurations, and techniques discussed above with respect to the centrifugation step (104) in connection with total dietary fiber determination. For example, a thermal gradient may be established between a container containing the dissolved dietary fiber solution and the centrifuge to help promote good pellet formation and separation between the insoluble fiber fraction in the pellet and the soluble fiber fraction in the supernatant liquid.

After centrifuging the dissolved dietary fiber solution to produce the pellet containing insoluble dietary fiber and the supernatant liquid containing soluble dietary fiber (118), the pellet is separated from the supernatant liquid (120). Separation can be performed using any of the techniques and equipment configurations discussed above with respect to the separation step (106) in connection with total dietary fiber determination. For example, the supernatant liquid may be extracted from the pellet via aspiration, e.g., using a hardware apparatus configured as shown in FIG. 2.

If it is desired to determine the content of water-insoluble dietary fiber in the pellet generated via centrifugation of the dietary fiber solution, the pellet is optionally de-fatted using an organic solvent following any of the techniques and equipment configurations discussed above with respect to de-fatting step (108) in connection with total dietary fiber determination. For example, the pellet containing water-insoluble dietary fiber may be mechanically broken down and intermixed with an organic solvent to yield a dissolved fat solution. The dissolved fat solution can then be centrifuged (124) to yield a second pellet that is de-fatted and contains water-insoluble dietary fiber and a second supernatant liquid formed of organic liquid containing the dissolved fat. The second pellet can be separated from the second supernatant liquid (126) and dried (128) to produce a dried solid containing water-insoluble dietary fiber using the techniques and equipment configurations discussed above with respect to separation step (112) and drying step (114) in connection with total dietary fiber determination. For example, the second supernatant liquid may be extracted from the second pellet via aspiration and the pellet then dried via freeze drying. The dried solid provided by the pellet containing water-insoluble dietary fiber can then be analyzed to determine insoluble dietary fiber content, as will be discussed in connection with FIG. 3.

Additionally or alternatively, if it is desired to determine the content of water-soluble dietary fiber in the supernatant liquid generated via centrifugation of the dietary fiber solution, the water-soluble dietary fiber may be precipitated from the supernatant liquid (132). The water-soluble dietary fiber can be precipitated from the supernatant liquid using the techniques and equipment configurations discussed above with respect to precipitation step (102) in connection with total dietary fiber determination. For example, the supernatant liquid containing the water-soluble dietary fiber may be mixed with a precipitating agent, such as an alcohol (e.g., ethanol), to precipitate the water-soluble dietary fiber out of the supernatant liquid. The supernatant liquid containing the precipitated water-soluble dietary fiber may then be centrifuged (134) to produce a third pellet and a third supernatant liquid. The third pellet can contain the water-soluble dietary fiber (and may also contain contaminants) while the third supernatant liquid can contain non-dietary fiber components dissolutted from the original fiber-containing sample, residual dissolution agent, and/or residual precipitating agent.

The third pellet containing water-soluble dietary fiber can be separated from the third supernatant liquid (136) using the techniques and equipment configurations discussed above with respect to separation step (112) in connection with total dietary fiber determination. For example, the third supernatant liquid may be extracted from the third pellet via aspiration, e.g., using an equipment configuration as described in connection with FIG. 2.

After separating the third pellet from the third supernatant liquid, the third pellet is optionally de-fatted using the techniques and equipment configurations discussed above with respect to de-fatting step (108) in connection with total dietary fiber determination. In some applications, the third pellet containing water-soluble dietary fiber may not tightly bind any residual fat. As a result, the third pellet may be rinsed with an organic solvent without fully immersing the pellet in the solvent, causing any fat contained in the pellet to dissolve and carry away in the solvent. In other applications where residual fat is more tightly bound with the third pellet, the third pellet can be mechanically mixed with the organic solvent, causing the pellet to physically break apart and intermix with the solvent. If this more invasive de-fatting technique is performed, the resulting dissolved fat solution may be centrifuged to produce a de-fatted pellet and supernatant liquid using the techniques and equipment configurations discussed above with respect to centrifugation step (110) in connection with total dietary fiber determination. The de-fatted pellet can then be separated from the supernatant liquid using the further techniques and equipment configurations discussed above with respect to separation step (112) in connection with total dietary fiber determination.

Independent of the specific technique used to de-fat the third pellet (138) (assuming any de-fatting technique is performed at all), a resulting pellet containing water-soluble dietary fiber may be dried (140) to produce a dried solid containing water-soluble dietary fiber. The pellet can be dried using the techniques and equipment configurations discussed above with respect to drying step (114) in connection with total dietary fiber determination. For example, the third pellet may be dried via freeze drying. The dried solid provided by the pellet containing water-soluble dietary fiber can then be analyzed to determine insoluble dietary fiber content, as will be discussed in connection with FIG. 3.

During performance of the technique of FIG. 1, a dietary fiber-containing sample and the dietary fiber-containing pellet(s) and/or supernatant liquid(s) generated therefrom can be transferred from one container to a different container between each step of the techniques. Alternatively, a dietary fiber-containing sample and the dietary fiber-containing pellet(s) and/or supernatant liquid(s) generated therefrom can remain in the same container during performance of two or more steps of the technique. As one example, a dietary fiber-containing sample may be placed in a container configured (e.g., sized and/or shaped) to be inserted into a centrifuge. The dietary fiber-containing sample can be dissolutted in the container to produce a dietary fiber solution (100). Water-soluble dietary fiber can be precipitated in the container by adding a precipitating agent to the container (102) and the container then centrifuged (104). Afterwards, supernatant liquid generated during centrifugation can be aspirated out of the container (106), leaving the corresponding pellet in same centrifuge container for further processing. If desired, de-fatting (108), centrifugation (110), separation (112), and/or drying (114) can also be performed while dietary fiber remains in the same centrifuge container. Reducing or eliminating physical transfer of the dietary fiber from one container to another container during analysis may reduce or eliminate dietary fiber loss that can otherwise lead to underreporting of the true amount of dietary fiber in a sample.

Notwithstanding whether one or more containers are used during execution of the technique of FIG. 1, any suitable size container(s) can be used. Without wishing to be bound by any particular theory, it is believed that using comparatively larger container(s) may show better dietary fiber yield for a given sample as compared to when the sample is processed using a comparatively smaller container. The smaller internal surface area/volume ratio of the larger container can reduce the amount of dietary that is lost when dietary fiber contacts and adheres to the wall surface of the container. In some examples, the technique of FIG. 1 is executed using a container(s) having a volume of at least 250 milliliters, such as at least 500 milliliters.

Although the technique of FIG. 1 has generally been described in connection with a dietary fiber-containing sample that is processed to separate dietary fiber in the sample from other non-dietary fiber components, in practice, the technique may be performed at least twice. For example, the technique may be performed once on a dietary fiber-containing sample, the dietary fiber content of which is desired to be quantified. The technique may be performed a second time using identical reagents, volumes, and processing parameters but without the presence of the dietary fiber-containing sample. This can provide a "blank" sample used to determine the weight of residual processing agents in the isolated dietary fiber-containing solid, as well as the degree of drying of the solid in the sample container. This residual weight can be subtracted from the determined weight of the dietary fiber to provide a true dietary fiber weight measurement.

Figure 3:
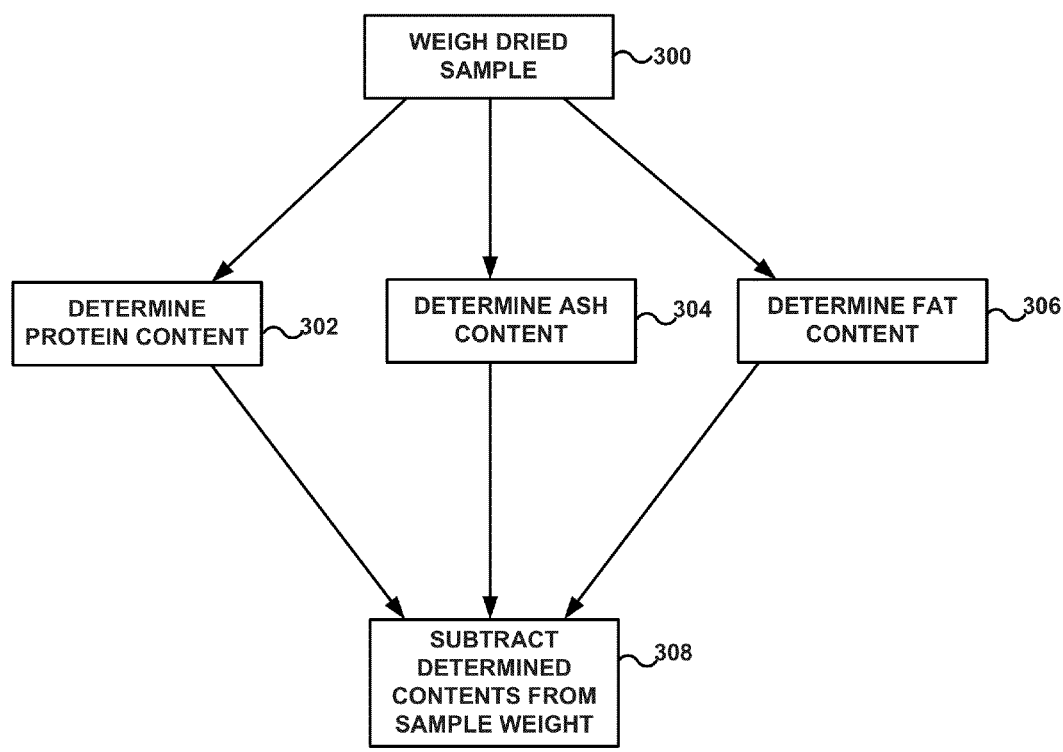
FIG. 3 is a flow diagram illustrating an example process for determining the dietary fiber content of a solid containing isolated dietary fiber.

FIG. 3 is a flow diagram illustrating an example process for determining the dietary fiber content of a solid containing isolated dietary fiber. The solid containing the isolated dietary fiber can be generated following various isolation steps discussed above with respect to FIG. 1. The solid may contain total dietary fiber from an original dietary fiber-containing sample (116 in FIG. 1), water-insoluble dietary fiber (130 in FIG. 1), or water-soluble dietary fiber (142 in FIG. 1). In general, the solid may be predominately dietary fiber but may still contain residual contaminants that need to be accounted for when determining the weight of the dietary fiber. For example, the solid may contain residual protein, residual fat, and/or ash that was not removed during isolation of the solid.

In some examples, the dietary fiber content of the solid is determined by first determining the content of non-dietary fiber components in the solid. The dietary fiber content of the fiber in the solid can then be determined based on the non-dietary fiber content. For example, the weight of non-dietary fiber components in the solid can be measured. The measured weight of the non-dietary fiber components can be subtracted from the total weight of the solid. Assuming that all the remaining weight in the solid is attributable to dietary fiber, the difference between the total weight of the solid and the weight of the non-dietary fiber components in the solid can be reported as the dietary fiber weight. In this manner, gravimetric difference between a total weight of the solid and a weight of non-dietary fiber components can reveal the dietary fiber content of the sample. The dietary fiber content may be reported as an absolute weight or as a weight percentage of the original dietary fiber-containing sample from which fiber was isolated using the technique of FIG. 1.

In the technique of FIG. 3, the solid containing isolated dietary fiber is weighed (300) to determine a total weight of the solid (e.g., pellet), which can include the weight of both dietary fiber and residual contaminants. Typical residual contaminants include proteins and ash. Accordingly, in FIG. 3, a first portion of the solid is analyzed to determine a protein content in the solid (302), and a second portion of the solid is analyzed to determine an ash content in the solid (304). Prior to extracting portions of the solid for analysis of individual contaminants, the solid may be homogenized by mechanical crushing or blending the solid. For example, a solid pellet containing isolated dietary fiber and produced in accordance with the technique of FIG. 1 can be physically crushed and the resulting crushed solid intermixed until the solid is compositionally homogeneous. Homogenizing the solid may be useful to ensure that each portion extracted for analysis of an individual contaminant is compositionally identical to each other portion extracted from the sample.

The protein content in the solid (302) can be determined using any acceptable analytical technique. In one example, the first portion of the solid is subject to amino acid analysis to determine the protein content in the solid. In another example, the first portion of the solid is analyzed to determine the nitrogen content of the solid. For example, the first portion of the solid may be subject to either Dumas combustion or Kjeldahl analysis to determine the nitrogen content in the solid. In such examples, all nitrogen in the solid may be assumed to be attributable to protein in the solid. Accordingly, the protein content in the first portion of the solid can be determined and, with knowledge of the weight of the first portion relative to the weight of total solid, the protein content of the total solid determined.

The ash content in the solid (304) can also be determined using acceptable analytical techniques. In general, ash refers to any residual material remaining in a sample after the sample is subject to high temperature heating. The high temperature heating can combust and decompose organic species in the material, typically leaving only inorganic materials, such as inorganic salts, that may be present in the material. In one example, the second portion of the solid is subject to ash analysis by heating the portion to a temperature ranging from 500 degrees Celsius to 650 degrees Celsius, such as approximately 580 degrees Celsius. The residual material remaining after the heating process is weighed and established as the ash content of the second portion. With knowledge of the weight of the second portion relative to the weight of total solid, the ash content of the total solid determined.

If further contaminants beyond protein and ash are believed to be present in the solid containing isolated dietary fiber, one or more additional portions can be extracted from the solid and analyzed to determine the content of those additional individual contaminants believed to be present. In the example of FIG. 3, for example, a third portion of the solid is analyzed to determine a fat content in the solid (306). Such analysis may be useful in applications where fat is believed to be present in the original dietary fiber-containing sample but the sample was not subject to de-fatting (108, 122, and/or 138 in FIG. 1) when preparing the solid containing the isolated dietary fiber. The fat content of the solid can be measured by gas chromatography using AOAC 996.06, or extraction of fat by organic solvent with gravimetric determination. With knowledge of the weight of the third portion relative to the weight of total solid, the fat content of the total solid determined.

After determining the content of non-dietary fiber components (e.g., protein, ash, fat) in the solid under analysis, the dietary fiber content of the solid can be calculated by subtracting the weight of the non-dietary fiber components from the total weight of the solid (308). For example, the determined weight of the protein and the determined weight of the ash can be subtracted from the total weight of the solid. If measured, the determined weight of the fat and any other contaminants can also be subtracted from the total weight of the solid. In some examples, the weight of the "blank" sample corresponding to the weight of residual processing agents is also subtracted from the total weight of the solid. The calculated difference establishes the content (e.g., weight) of the dietary fiber in the solid and, correspondingly, the original dietary fiber-containing sample. Depending on the isolation technique performed in accordance with FIG. 1, the determined dietary fiber content may be the total dietary fiber content, the water-insoluble dietary fiber content, or the water-soluble dietary fiber content. If the water-insoluble dietary fiber content is determined separately from the water-soluble dietary fiber content, the water-insoluble dietary fiber content and water-soluble dietary fiber content can be summed to give a calculated total dietary fiber value.

Figure 4:
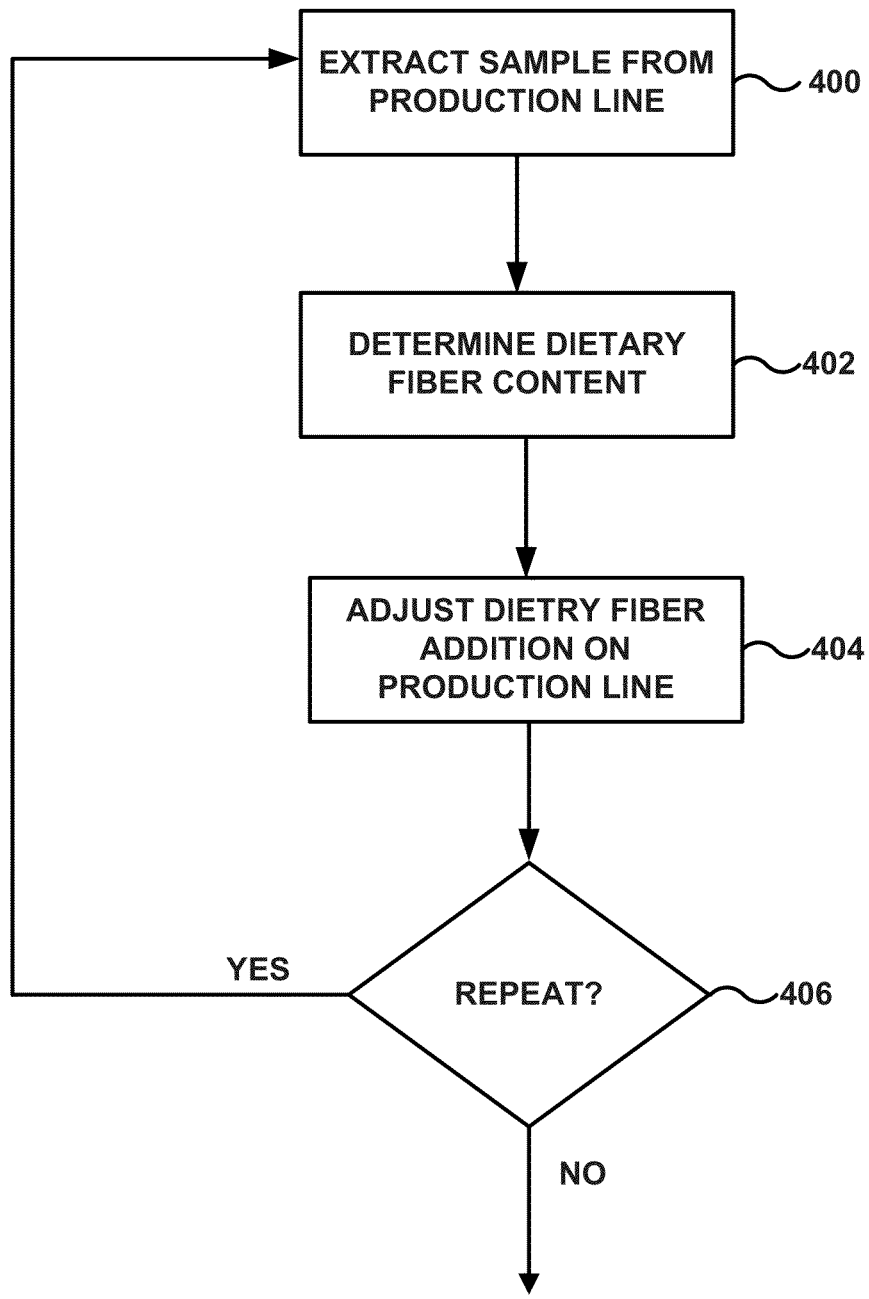
FIG. 4 is a flow diagram illustrating an example technique by which a commercial manufacture can control dietary fiber addition to a product based on accurate quantification of the product's true dietary fiber content.

For commercial manufacturers of dietary fiber-containing products, the ability to accurately measure the true dietary fiber content of the products can enable tight control over the amount of dietary fiber added to the products and cost savings where over addition can be reduced or eliminated. FIG. 4 is a flow diagram illustrating an example technique by which a commercial manufacture can control dietary fiber addition to a product based on accurate quantification of the product's true dietary fiber content.

As shown in FIG. 4, the example technique includes extracting a sample of a dietary fiber-containing product from a commercial production line (400). The commercial production line may produce a dietary fiber-containing product suitable for consumption, such as a food, beverage, or supplement. During manufacture of the dietary fiber-containing product, dietary fiber extracted from a fiber-containing source may be added to enhance the dietary fiber content of the product.

The extracted dietary fiber sample is analyzed to determine a dietary fiber content of the product (402). For example, the extracted dietary fiber sample may be analyzed to determine a total dietary fiber content, a water-insoluble dietary fiber content, and/or a water-soluble dietary fiber content following the techniques of FIGS. 1 and 3 discussed above. With knowledge of the dietary fiber content in the extracted dietary fiber sample, the amount of dietary fiber added to the product on the production line can be adjusted (404). In some examples, the amount of dietary fiber added to the product on the production line is reduced after determining that the amount of dietary fiber in the product exceeds a target threshold. The process can be repeated (406) until the amount of dietary fiber in the product meets a target amount set by the manufacturer.

The disclosure provides in some embodiments the benefits of recovering the full amount of dietary fiber present in a sample. Current dietary fiber methodologies lose to waste significant amounts of dietary fiber due to the incompleteness of capture by the filtering systems employed. The use of centrifugation and other methodologies allows more efficient and consistent recovery of dietary fiber components.

A sample may be enzymatically and/or chemically digested in accordance with the methodologies accepted by regulatory bodies directly in a centrifuge tube or bottle. In the case of enzymatic digest, the reaction can be stopped by heat denaturation of the enzymes to provide more consistency between sample to sample processing.

In one embodiment for determination of Total Dietary Fiber (TDF) only, the digested sample solution is brought to a concentration of 85% Reagent Alcohol and chilled for at least 3 hours at −20° C. to precipitate soluble dietary fiber. The entirety of the chilled mixture is incubated at 60° C. for 5 minutes. The solution is centrifuged at 13,700×g for 30 minutes at 4° C. in a 500 mL polypropylene copolymer bottle to capture all of the fiber. The supernatant containing low-molecular-weight resistant oligosaccharides (maltodextrins) is removed from the pellet of TDF by aspiration and may in some circumstance be quantified by HPLC. The fat in the pellet containing the total dietary fiber is removed (de-fatted) by stirring at 60° C. with a solution of 2:1 (v/v) acetone/methanol. The de-fatted TDF is centrifuged at 13,700×g for 30 minutes at 25° C. in a centrifuge outfitted with an inert nitrogen atmosphere to minimize flammability. The organic solvent supernatant containing the fat is aspirated off and the remaining pellet is freeze-dried for 16 hours. The freeze-dried pellet is homogenized and transferred to a capped storage tube. One aliquot of the homogenized, dried pellet is assayed for total protein by Dumas combustion or Kjeldahl and the remainder of the pellet is assayed for total ash. The protein, ash, and blank control results are subtracted from the dried pellet weight to give the Total Dietary Fiber in the original sample.

In another embodiment for determination of Insoluble Dietary Fiber (IDF) and Soluble Dietary Fiber (SDF), the enzyme digested sample solution is first centrifuged at 81,800×g for 30 minutes at 15° C. in a 50 mL polyallomer oakridge-style tube to separate the IDF (pellet) from the SDF (supernatant). The supernatant containing the SDF is aspirated off of the top of the pellet and transferred to a 500 mL polypropylene copolymer centrifuge bottle where it is brought to a concentration of 85% Reagent Alcohol and chilled for at least 3 hours at −20° C. to precipitate soluble dietary fiber. The pellet containing the IDF is de-fatted with stirring at 60° C. with a solution of 2:1 (v/v) acetone/methanol. The de-fatted IDF is centrifuged at 81,800×g for 30 minutes at 25° C. in a centrifuge outfitted with an inert nitrogen atmosphere to minimize flammability. The organic solvent supernatant containing the fat is aspirated off and the remaining IDF is freeze-dried for 16 hours. The freeze-dried IDF is homogenized and transferred to a capped storage tube. One aliquot of the homogenized, dried IDF is assayed for total protein by Dumas combustion or Kjeldahl and the remainder of the pellet is assayed for total ash. The protein, ash, and blank control results are subtracted from the dried IDF weight to give the IDF in the original sample.

Following the 3 hour precipitation of the SDF above, the SDF mixture is centrifuged at 13,700×g for 30 minutes at 4° C. The supernatant containing low-molecular-weight resistant oligosaccharides is removed from the pellet of SDF by aspiration and may in some circumstance be quantified by HPLC. The SDF pellet is de-fatted by washing with a 2:1 (v/v) acetone/methanol solution. The organic solvent supernatant containing the fat is aspirated off and the remaining SDF is freeze-dried for 16 hours. The freeze-dried SDF is homogenized and transferred to a capped storage tube. One aliquot of the homogenized, dried SDF is assayed for total protein by Dumas combustion or Kjeldahl and the other is assayed for total ash. The protein, ash, and blank control results are subtracted from the dried IDF weight to give the IDF in the original sample. The IDF and SDF values can be summed to give a calculated Total Dietary Fiber value.

In another embodiment, the amount of protein determined by Dumas combustion is converted to the equivalent amount of protein by Kjeldahl or protein by amino acid analysis by use of an equation that provides the direct relationship between these methodologies. This allows better conformity to regulatory and accepted practices in different jurisdictions around the world.

The following are example laboratory protocols that may be executed to determine the dietary fiber content of a sample.

Dietary Fiber, Insoluble, Soluble and Total, Based on AOAC 991.43 Enzymatic-Gravimetric (Modified with Centrifugation)

This method can determine the amount of soluble (SDF), insoluble (IDF), total dietary fiber (TDF) and resistant oligosaccharides (RO) in food products and ingredients.

Scope:

This method may be applicable to processed foods, grains, cereal products, fruits and vegetables.

Range:

0.1-100%
TDF LOQ=0.1%
IDF LOQ=0.1%
SDF LOQ=0.2%
TDF Calculated (IDF+SDF) LOQ=0.2%

NOTE: Soluble fiber residue weights less than 0.0010 g are below the LOQ of 0.2% and therefore do not need to be processed for protein and ash (protein and ash should be assumed as 0% for this SDF residue weight range). Total and insoluble fiber residue weights less than 0.0005 g are below the LOQ of 0.1% and therefore do not need to be processed for protein and ash (protein and ash should be assumed as 0% for this TDF and IDF residue weight range).

Principle:

Homogeneous samples are incubated at 95 to 100° C. to gelatinize starch, in the presence of a heat-stable α-amylase which digests non-dietary fiber polysaccharides. After cooling to 60° C., further enzymatic digestion with protease and amyloglucosidase to digest protein and non-dietary fiber polysaccharides, respectively, is performed.

To determine Total Dietary Fiber (TDF) only, the digested sample solution is brought to a concentration of 85% Reagent Alcohol and chilled for at least three hours at −20° C. to precipitate soluble dietary fiber. The entirety of the chilled mixture is incubated at 60° C. for 5 min, and then centrifuged at 13,700×g for 30 min at 4° C. in a 500 mL polypropylene copolymer bottle to capture all of the fiber. The supernatant containing low-molecular-weight resistant oligosaccharides (maltodextrins) is removed from the pellet of TDF by aspiration and may in some circumstance be quantified by HPLC. The pellet containing the total dietary fiber is de-fatted by stirring at 60° C. with a solution of 2:1 (v/v) acetone/methanol. The de-fatted TDF is centrifuged at 13,700×g for 30 min at 25° C. in a centrifuge outfitted with an inert nitrogen atmosphere to minimize flammability. The organic solvent supernatant containing the fat is aspirated off and the remaining pellet is freeze-dried for 16 hours. The freeze-dried pellet is homogenized and transferred to a capped storage tube. One aliquot of the homogenized, dried pellet is assayed for total protein by Dumas combustion or Kjeldahl and the remainder of the pellet is assayed for total ash. The protein, ash, and blank control results are subtracted from the dried pellet weight to give the Total Dietary Fiber in the original sample.

To determine Insoluble Dietary Fiber (IDF) and Soluble Dietary Fiber (SDF), the enzyme digested sample solution is first centrifuged at 81,800×g for 30 min at 15° C. in a 50 mL polyallomer Oakridge tube to separate the IDF (pellet) from the SDF (supernatant). The supernatant containing the SDF is aspirated off of the top of the pellet and transferred to a 500 mL polypropylene copolymer centrifuge bottle where it is brought to a concentration of 85% Reagent Alcohol and chilled for at least 3 hours at −20° C. to precipitate soluble dietary fiber. The pellet containing the IDF is de-fatted with stirring at 60° C. with a solution of 2:1 (v/v) acetone/methanol. The de-fatted IDF is centrifuged at 81,800×g for 30 min at 25° C. in a centrifuge outfitted with an inert nitrogen atmosphere to minimize flammability. The organic solvent supernatant containing the fat is aspirated off and the remaining IDF is freeze-dried for 16 hours. The freeze-dried IDF is homogenized and transferred to a capped storage tube. One aliquot of the homogenized, dried IDF is assayed for total protein by Dumas combustion or Kjeldahl and the remainder of the pellet is assayed for total ash. The protein, ash, and blank control results are subtracted from the dried IDF weight to give the IDF in the original sample.

Following the 3 hour precipitation of the SDF above, the SDF mixture is centrifuged at 13,700×g for 30 min at 4° C. The supernatant containing low-molecular-weight resistant oligosaccharides is removed from the pellet of SDF by aspiration and may in some circumstance be quantified by HPLC. The SDF pellet is de-fatted by washing with a 2:1 (v/v) acetone/methanol solution. The organic solvent supernatant containing the fat is aspirated off and the remaining SDF is freeze-dried for 16 hours. The freeze-dried SDF is homogenized and transferred to a capped storage tube. One aliquot of the homogenized, dried SDF is assayed for total protein by Dumas combustion or Kjeldahl and the other is assayed for total ash. The protein, ash, and blank control results are subtracted from the dried SDF weight to give the SDF in the original sample.

The IDF and SDF values can be summed to give a calculated Total Dietary Fiber value.

Chemicals:

| | | |
|---|---|---|
| 1. | Acetone, AR Grade | VWR International Cat. No. MK244310 |
| 2. | Methanol, HPLC Grade | VWR International Cat. No. JT9093-3 |
| 3. | Algaecide | VWR International Cat. No. 54847-540 |
| 4. | Enzymes | Megazyme |
| | α-amylase (*B. licheniformis*) | Cat. No. E-BLAAM |
| | Protease (Subtilisin A) | Cat. No. E-BSPRT |
| | Amyloglucosidase (*A. niger*) | Cat. No. E-AMGDF 353-1-286-1220 www.megazyme.com |
| 5. | Anhydrous Reagent Alcohol (90% ethanol, 5% methanol, 5% IPA) | Hawkins, Inc. Item No. 38783 612-617-8630 www.hawkinsinc.com |
| 6. | Hydrochloric acid solution 1.0N | VWR International Cat. No. BDH3202-1 |
| 7. | Hydrochloric acid solution 0.5N | VWR International Cat. No. BDH3201-1 |
| 8. | MES hydrate 2-(N-Morpholino)ethanesulfonic acid hydrate | Sigma-Aldrich Cat. No. M8250 800-325-3010 www.sigmaaldrich.com |
| 9. | pH buffers Buffer, pH 4.00 Buffer, pH 7.00 Buffer, pH 10.00 | Fisher Scientific Cat. No. SB101 500 Cat. No. SB107 500 Cat. No. SB115 500 800-766-7000 www.fishersci.com |
| 10. | pH electrode solutions Storage Solution, 3% KCl Filling Solution, ROSS | VWR International Cat. No. 34108-041 Cat. No. 34107-413 |
| 11. | Sodium hydroxide solution 1.0N | VWR International Cat. No. MK469360 |
| 12. | Sodium hydroxide solution, 0.5N | VWR International Cat. No. BDH3221-1 |
| 13. | Gold Pump Oil | VWR International Cat. No. 54970-662 |
| 14. | Trizma base Tris(hydroxymethyl)aminomethane | Sigma-Aldrich Cat. No. T1503 800-325-3010 www.sigmaaldrich.com |
| 15. | SDS Sodium dodecyl sulfate | Sigma-Aldrich Cat. No. L3771 |

Apparatus:

| | | |
|---|---|---|
| 1. | Balance-Analytical, reads to ±0.01 mg<br>Mettler Toledo XP205 with Integrable AntiStatic Kit | Mettler Toledo<br>us.mt.com/us/en/home.html |
| 2. | Boiling water bath-to maintain 95-100° C. | VWR International with Cover<br>Cat. No. Boekel BB-2800 |
| 3. | Constant temperature water bath Adjustable to 60° C. with immersion circulator, Haake DC30 | Fisher Scientific<br>Cat. No 13-874-364 |
| 4. | Graduated Cylinders<br>250 mL, Nalgene<br>250 mL, glass<br>500 mL, glass<br>2000 mL, glass<br>4000 mL, Nalgene | VWR International<br>Cat. No. 24780-108<br>Cat. No. 24709-759<br>Cat. No. 24709-760<br>Cat. No. 89001-124<br>Cat. No. 24776-188 |
| 5. | Miracloth | VWR International<br>Cat. No. 80058-394 |
| 6. | Disposable Microfuge Tubes, 2 mL | VWR International<br>Cat. No. 89129-818 |
| 7. | Double Spinfin Stir Bars | VWR International<br>Cat. No. 58948-998 |
| 8. | Single-channel Electronic Pipette<br>15-300 μL<br>50-1000 μL | VWR International<br>Cat. No. 89133-428<br>Cat. No. 89133-430 |
| 9. | Lo Retention Pipette Tips<br>2-200 μL<br>50-1000 μL | VWR International<br>Cat. No. 89093-238<br>Cat. No. 89093-240 |
| 10. | pH Meter<br>Metrohm 780 | Metrohm<br>Cat. No. 2.780.0010<br>www.metrohmusa.com<br>1-800-645-3050 |
| 11. | pH electrode<br>Orion Microprobe | Fisher Scientific<br>Cat. No. 13642800 |
| 12. | Auto Pipette<br>Repeater Stream<br>Combitips Plus tips, Sterile 5 mL | Eppendorf North America<br>Cat. No. 022460803<br>www.eppendorfna.com<br>800-645-3050 |
| 13. | 9-place Magnetic stirrer | VWR International<br>Cat. No. 12621-042 |
| 14. | Polygon Stir Bars, ⅜ × 1" | VWR International<br>Cat. No. 58948-983 |
| 15. | Aluminum Foil | VWR International<br>Cat. No. 29952-040 |
| 16. | Magnet<br>Small<br>Medium | VWR International<br>Cat. No. 36922-007<br>Cat. No. 36923-008 |
| 17. | Desiccators<br>Plastic<br>Acrylic Desiccator Cabinet (12 × 12 × 12")<br>Acrylic Desiccator Cabinet (18 × 12 × 12") | VWR International<br>Cat. No. 24988-197<br>Cat. No. 24987-053<br>Cat. No. 24987-056 |
| 18. | Coffee Grinder<br>Krupps 203 | Goodman's<br>Cat. No. KR-203-70<br>www.goodmans.net |
| 19. | Osterizer Blender<br>Model 4108<br>8 oz blender cups | Goodman's<br>Cat. No. OS-4108<br>Cat. No. OS-090-6PK |
| 20. | Dispensettes<br>5-50 mL<br>10-100 mL | VWR International<br>Cat. No. 18901-144<br>Cat. No. 18901-146 |
| 21. | Test Tube Racks<br>8-Well Centrifuge Tube Rack<br>Test Tube Rack, 24 spots<br>50 mL Centrifuge Tube Racks, 16 spots<br>Microfuge Tube Racks, 80 spots | VWR International<br>Cat. No. 82024-452<br>Cat. No. 89215-802<br>Cat. No. 21008-486<br>Cat. No. 30128-282 |
| 22. | High Form Porcelain Crucibles, 1.3 mL | VWR International<br>Cat. No. 89037-986 |
| 23. | High Form Porcelain Crucibles, 5 mL | VWR International<br>Cat. No. 89037-988 |
| 24. | Analog Vortex Mixer | VWR International<br>Cat. No. 58816-121 |
| 25. | Tubing:<br>Silicone, 8 mm | Wheaton Scientific Products<br>Cat. No. 374308 |

-continued

| | | |
|---|---|---|
| | Viton, 6 mm | Cat. No. 374318<br>www.wheatonsci.com<br>800-225-1437 |
| 26. | High Performance Centrifuge<br>Avanti J-26XPI | Beckman-Coulter<br>Cat. No. 393127 |
| 27. | Avanti J-26XPI Centrifuge Rotors<br>JA-10<br>JA-30.50 Ti | Beckman-Coulter<br>Cat. No. 369687<br>Cat. No. 363420 |
| 28. | 50 mL Polyallomer Centrifuge Tube | Beckman-Coulter<br>Cat. No. 357001 |
| 29. | 500 mL Polypropylene Copolymer Bottle | VWR International<br>Cat. No. 21010-636 |
| 30. | Rubber Policeman | VWR International<br>Cat. No. 53801-008 |
| 31. | Plastic Spatula | VWR International<br>Cat. No. 53803-116 |
| 32. | Disposable Funnels | VWR International<br>Cat. No. 30246-021 |
| 33. | Muffle Furnace<br>Capable of maintaining 580 ± 5° C. | VWR International<br>Cat. No. 30620-106 |
| 34. | Freeze-Dryer | SP Scientific<br>Cat. No. FM35EL |
| 35. | Shell Freezer | SP Scientific<br>Cat. No. FMEL2 |
| 36. | Freeze-Dryer Vessels<br>600 mL<br>1200 mL<br>¾" Port Adaptor for Freeze-Dryer Vessels<br>Filter Paper for Freeze-Dryer Vessels | SP Industries<br>Cat. No. 312934<br>Cat. No. 118273<br>Cat. No. 177923<br>Cat. No. 172478 |
| 37. | Branson Ultra-Sonic Bath | Fisher Scientific<br>Cat. No. 15-336-133<br>Branson Ultrasonics<br>Cat. No. CPX-952-519R |
| 38. | 4-channel alarm/stopwatch | VWR International<br>Cat. No. 62344-641 |
| 39. | Thermometers<br>Easy-Read<br>Traceable, lollipop<br>Traceable, probe/cable | VWR International<br>Cat. No. 33600-012<br>Cat. No. 12777-842<br>Cat. No. 46610-024 |
| 40. | Wash Bottles<br>500 mL, acetone/methanol<br>500 mL, water<br>500 mL, ethanol | VWR International<br>Cat. No. 16649-900<br>Cat. No. 16651-187<br>Cat. No. 16649-900 |
| 41. | Sample Cups, 4 oz | VWR International<br>Cat. No. 16126-022 |
| 42. | Volumetric Flask<br>100 mL | VWR International<br>Cat. No. 89079-228 |
| 43. | Water purification system<br>PURELAB Ultra | ELGA Labwater<br>www.elgalabwater.com<br>800-875-7873 |
| 44. | Disposable Syringe | VWR International<br>Cat. No. BD309604 |
| 45. | Large Orifice Pipet Tips, 101-1000 μL | Fisher Scientific<br>Cat. No. 02-707-141 |
| 46. | Polypropylene Culture Tubes, nonsterile, 5 mL | VWR International<br>Cat. No. 20170-579 |
| 47. | Dual-Position Caps, Polyethylene, 12 × 75 mm | VWR International<br>Cat. No. 60818-463 |

Reagents:
1. MES-TRIS buffer, pH 8.2. Using a 3-place balance weigh 19.520±0.003 g MES and 12.200±0.003 g TRIZMA. Quantitatively transfer using nanopure water to an empty 2 L graduated cylinder. Bring volume to approximately 1900 mL with nanopure water and a stir bar. Add 40 mL 1.0 N NaOH. Mix thoroughly on stir plate. Adjust to pH 8.20 using 1.0 N NaOH or 1.0 N HCl. Remove stir bar and dilute to 2000 mL with nanopure water and mix well. Can be stored at room temperature for up to two weeks. Record preparation in reagent log book. Preparing up to 4 L of buffer at a time is acceptable by doubling all volumes and weights.
2. 1% SDS. Using a 3-place balance weigh 1.000±0.003 g SDS. Quantitatively transfer using nanopure water to a 100 mL volumetric flask, bring the volume to approximately 80 mL and add a stir bar. Stir until completely dissolved. Remove stir bar and bring to 100 mL. Can be stored at room temperature for two weeks. Record preparation in reagent log book.

3. 2:1 (v/v) Acetone/Methanol (de-fatting solvent). Using a 4 L graduated cylinder, measure 2400 mL of acetone. In the same graduated cylinder, add methanol to bring the total volume up to the 3600 mL mark. Transfer solvent to proper storage container. Can be stored in the flammable cabinet at room temperature for up to six months. Record preparation in reagent log book.

4. Fructozyme, ≥200 U/mL. Depending on the activity of the enzyme lot, calculate volume of nanopure water needed to achieve the stated concentration using the equation provided below. Using this volume of nanopure water, quantitatively transfer the contents of the enzyme bottle to an appropriate volumetric. Stopper and invert to mix well. Store at 0-10° C. for up to one year. Record preparation in reagent logbook.

$$\left[\frac{(Uendo + Uexo)(v)}{200 \text{ U/mL}}\right] - v = V$$

v=volume of enzyme in original bottle in mL
Uendo=Units of endolnulinase per mL in original enzyme bottle
Uexo=Units of exolnulinase per mL in original enzyme bottle
V=mL nanopure water to be added to the dilution Determination of Insoluble (IDF) and Soluble (SDF) Dietary Fiber 1. Determine the tare weight of all 50 mL polyallomer centrifuge tubes (50PCT) to be used for collecting IDF residue and all 500 mL polypropylene copolymer bottles (500PCB) to be used for collecting SDF residue to four decimal places.
2. Designate one 50PCT and one 500PCB as a blank to which no sample will be added but which will be exposed to all reagents and processes of the method.
3. Weigh up samples into 50PCTs. Sample weight should be 0.500±0.005 g. Record the exact weight.
   For high moisture samples (yogurt, soups, etc.), weigh up 2.000±0.005 g.
   For very high moisture samples (fruit juice, etc.) weigh up 5.000±0.005 g.
   For a fruit juice or any sample where higher than typical acidity is suspected, check the pH of the sample in the buffer solution before adding α-amylase and adjust to 8.1-8.3 using dilute NaOH and HCl.
   For psyllium husk-containing products, weigh up 0.100 g±0.005 g. This is done to maintain consistency with the Code of Federal Regulations 21CFR101.81 on measurement of psyllium using a modification of the Association of Official Analytical Chemists' International (AOAC's) method for soluble dietary fiber (991.43) described by Lee et al., "Determination of Soluble and Insoluble Dietary Fiber in Psyllium-containing Cereal Products," Journal of the AOAC International, 78 (No. 3):724-729, 1995.
   NOTE: Samples with fat that causes inaccurate fiber results should be de-fatted before weighing.
4. Add a double spinfin stir bar to each 50PCT and place in stainless steel rack with inserts for 50PCTs on magnetic stir plate.
5. Add 20 mL MES-TRIS-buffer solution to each 50PCT via bottle-top dispenser. Stir on magnetic stir plate for 5 minutes.
6. Add 25 μL α-amylase solution to each tube via electronic pipette, on dispense mode, and screw caps on tubes a quarter turn. Move the rack containing all of the samples to boiling bath (97.5±2.5° C.) and incubate for 25 minutes. Ensure that the water level in the bath is above the sample volume in the bottle.
7. After 25 minutes of incubation in the boiling water bath, remove rack from boiling water bath. Place rack containing samples in 60±2° C. bath. Start stirring. Set timer to cool for 10 minutes. CAUTION: Be sure to wear proper PPE while removing rack from boiling bath and avoid dripping water from rack in walkways.
8. Remove the caps and add 50 μL protease solution to each 50PCT via electronic pipette, on dispense mode. Start the timer for 30 minutes. For each individual sample, screw the cap back on the tube, vortex until all sample is suspended, and resume incubation with stirring at 60±2° C. Make sure all caps are loose when placed into 60±2° C. bath after vortexing.
9. Remove the caps and dispense 1.4 mL 1.0 N HCl into tubes, via repeater pipette, while stirring. Adjust pH to 4.0-4.7 using 0.5 N NaOH/HCl or 1.0 N NaOH/HCl. Conservatively rinse the pH probe with 50-60° C. nanopure water into the corresponding 50PCT.
10. Add 150 μL amyloglucosidase solution to each 50PCT via electronic pipette, on dispense mode, while stirring. Start the timer for 30 minutes. For each individual sample, screw the cap back on the tube, vortex until all sample is suspended, and resume incubation with stirring at 60±2° C. Make sure all caps are loose when placed into 60±2° C. bath after vortexing.
11. Remove rack containing 50PCTs from 60±2° C. bath. Place entire rack in boiling bath (97.5±2.5° C.). Incubate for 20 minutes. The purpose of this step is to denature all of the enzymes and stop any further digestion.
12. Remove rack containing 50PCTs from the boiling bath.

Part A: Determination of Insoluble Dietary Fiber (IDF)

1. While 50PCTs are still warm/hot from step 12 above, remove stir bars from each tube and rinse with nanopure water back into 50PCT. Bring total weight of 50PCT with cap and insert to approximately 43 g with nanopure water to assure tube is at proper volume for safe centrifugation. Balance the 50PCTs along with their caps and inserts in pairs within ±0.5 g.
2. Place capped 50PCTs back in rack and into 60±2° C. water bath for at least 10 minutes. Remove from bath, quickly dry the outside of each tube, and proceed immediately to centrifugation.
3. Place the 50PCTs in the tempered JA-30.50 rotor with each balanced pair on the opposite sides of the rotor, symmetrically directly across from one another. Centrifuge according to established parameters.
4. Place 500PCB in the "narrow tube" aspirator jar corresponding to the sample number in the 50PCT to be processed.
5. Carefully remove the first 50PCT from the rotor. Use the aspirator to transfer the supernatant from the 50PCT to the 500PCB. Be careful not to transfer pellet particles. Once the supernatant has been removed, flush the aspirator tube with a small amount of nanopure water into the 500PCB. When finished, remove the cap insert, screw the cap back onto the 50PCT, and set the tube aside. Repeat steps 4-5 for each individual sample.

6. De-fatting of IDF Pellet:
   a. Add a double spinfin stir bar to each 50PCT, and screw the cap back on.
   b. Vortex each 50PCT until each pellet has been broken.
   c. Uncap each tube, and add approximately 30 mL of 2:1 (v/v) Acetone/Methanol (de-fatting solvent) to each 50PCT.
   d. Screw the cap back on each 50 PCT and vortex until the entire sample is suspended.
   e. Unscrew each cap so that it is loosened, but secure on the tube, and place into rack.
   f. Incubate at 60±2° C. for 30 minutes with constant stirring.
   g. Remove from water bath.
   h. Start a timer for 5 minutes.
      i. During the 5 minute cool down at room temperature, rinse both caps and stir bars back into 50PCT with the de-fatting solvent.
      ii. Add cap inserts to caps.
      iii. Bring total weight of 50PCT with cap and cap insert to approximately 40 g with de-fatting solvent to ensure bottle is at proper volume for safe centrifugation.
      iv. Balance 50PCT pairs (±0.5 g) with caps and cap inserts using de-fatting solvent.
7. Place the 50PCTs in the tempered JA-30.50 rotor with each balanced pair on the opposite sides of the rotor, directly across from one another. Flush the drum with nitrogen for 5 minutes. Centrifuge according to established parameters.
8. Place waste container in the "narrow tube" aspirator jar.
9. Carefully remove the first 50PCT from the rotor, and use the aspirator to remove the supernatant from the 50PCT. Once the supernatant has been removed, screw the cap back on the 50PCT. Repeat this step for each sample. Be careful not to transfer pellet particles.
10. Place each 50PCT containing the IDF pellet in a rack in the Shell-Freezer at −75° C. to −90° C. Incubate for at least 10 minutes.
11. Remove 50PCTs from Shell-Freezer. Wipe off excess ethanol. Place a small square of Miracloth and Miracloth holder cap onto the 50PCT. Quickly place 50PCTs in a 600 mL Freeze-Dryer flask and apply vacuum.
12. Allow to dry for 16 hours minimum on Freeze Dryer. Ensure that a blank is always included with each freeze dryer batch.
13. Remove the first Freeze-Dryer flask from the Freeze-Dryer. Weigh back each individual 50PCT, without cap or Miracloth to four decimal places.
14. Transfer the IDF pellet in each 50PCT to a labeled storage tube and homogenize.
15. Determine ash and protein content.

Part B: Determination of Soluble Dietary Fiber (SDF)
1. Bring the mass of each 500PCB to the bottle tare weight plus 30±0.1 g using nanopure water.
2. Add 180 mL of pre-chilled (approximately −20° C.) anhydrous reagent alcohol to each bottle. Add o-rings to caps. Be sure to mix the combined solution well by agitation/swirling of solution while cap is tightly on bottle.
3. Loosen caps and place in explosion proof −20±5° C. freezer for at least 3 hours. Loose caps are necessary so that pressure can equilibrate with temperature.
4. Balance all 500PCBs with corresponding caps and o-rings in pairs to ±0.5 g of each other using anhydrous reagent alcohol.
5. Place the 500PCB in the tempered JA-10 rotor with each balanced pair on the opposite sides of the rotor, symmetrically directly across from one another. Flush the drum with nitrogen for 5 minutes. Centrifuge according to established parameters.
6. Carefully remove the first 500PCB from the rotor. Use the "wide tube" aspirator to transfer the supernatant from the 500PCB to the aspirator receptacle. Flush the aspirator tube with a conservative amount of anhydrous reagent alcohol. Be careful not to transfer pellet particles. If RO is to be analyzed from sample, place "wide tube" aspirator stopper on top of round bottom flask for RO roto-evaporator.
7. Carefully add 10 mL of 2:1 (v/v) Acetone/Methanol (de-fatting solvent) to the bottle wall on the opposite side of the SDF pellet in the 500PCB. Using both hands, set the bottle on the benchtop at a 45° angle, pellet facing toward the ceiling, and make one complete rotation of the bottle to rinse the pellet. Rinse the sides of the bottle by carefully laying the bottle horizontal on the benchtop, pellet facing toward the ceiling, and making one complete rotation of the bottle.
8. Using the "narrow tube" aspirator, aspirate de-fatting solvent out of the 500PCB into a waste receptacle, being careful not to remove any particles from the pellet. Flush the aspirator tube with a small amount of nanopure water. Immediately screw the cap back on the bottle. Repeat steps 6-8 for each 500PCB.
9. Place each 500PCB containing the SDF pellet in the Shell-Freezer at −75° C. to −90° C. Incubate for at least 10 minutes.
10. Remove 500PCBs from Shell-Freezer. Wipe off excess ethanol, and remove the caps. Quickly place each 500PCB with corresponding cap, in a 1200 mL Freeze-Dryer flask with adapter and apply vacuum.
11. Allow to dry for 16 hours minimum on Freeze Dryer. Ensure that a blank is always included with each freeze dryer batch.
12. Remove the first Freeze-Dryer flask from the Freeze-Dryer. Weigh back each individual 500PCB, without cap to four decimal places.
13. Transfer SDF pellet to a labeled storage tube and homogenize.
14. Using the residue weights, determine ash and protein content by:

| Residue Weight Range (g) | Protocol |
| --- | --- |
| ≤0.00100 | Report Result < 0.2% |
| 0.00101–0.00600 | SDS Preparation |
|  | SDS Ash |
|  | SDS Protein |
| >0.00601 | Direct Ash |
|  | Direct Protein |

NOTE:
If unable to get a full 0.00601 g of residue out of the 500PCB, LOW RESIDUE WEIGHT METHOD FOR PREPARING PROTEIN AND ASH SAMPLES can be followed.

Determination of Total Dietary Fiber (TDF)
1. Determine the tare weight of all 500 mL polypropylene copolymer bottles (500PCB) to be used for collecting TDF to four decimal places.
2. Designate one 500PCB as a blank to which no sample will be added but which will be exposed to all reagents and processes of the method.
3. Weigh up samples into 500PCBs. Sample weight should be 0.500±0.005 g. Record the exact weight.
   For high moisture samples (yogurt, soups, etc.), weigh up 2.000±0.005 g.

For very high moisture samples (fruit juice, etc.) weigh up 5.000±0.005 g.

For a fruit juice or any sample where higher than typical acidity is suspected, check the pH of the sample in the buffer solution before adding α-amylase and adjust to 8.1-8.3 using dilute NaOH and HCl.

For psyllium husk-containing products, weigh up 0.100 g±0.005 g. This is done to maintain consistency with the Code of Federal Regulations 21CFR101.81 on measurement of psyllium using a modification of the Association of Official Analytical Chemists' International (AOAC's) method for soluble dietary fiber (991.43) described by Lee et al., "Determination of Soluble and Insoluble Dietary Fiber in Psyllium-containing Cereal Products," Journal of the AOAC International, 78 (No. 3):724-729, 1995.

NOTE: Samples with fat that causes inaccurate fiber results should be de-fatted before weighing.

4. Add a polygon stir bar to each 500PCB and place in stainless steel rack on magnetic stir plate.
5. Add 20 mL MES-TRIS-buffer solution to each 500PCB via bottle-top dispenser. Stir on magnetic stir plate for 5 minutes.
6. Add 25 μL α-amylase solution to each bottle via electronic pipette, on dispense mode, and screw caps (without o-rings) on bottles a quarter turn. Be sure that caps are loose on bottles to avoid pressure to build in bottle during incubation and subsequent contraction on cooling that will cause bottle to collapse. Move the rack containing all of the samples to boiling bath (97.5±2.5° C.) and incubate for 25 minutes. Ensure that the water level in the bath is above the sample volume in the bottle.
7. After 25 minutes of incubation in the boiling water bath, remove rack from boiling water bath. Place rack containing samples in 60±2° C. bath. Start stirring. Set timer to cool for 10 minutes. CAUTION: Be sure to wear proper PPE while removing rack from boiling bath and avoid dripping water from rack in walkways.
8. Remove the caps and add 50 μL protease solution to each 500PCB via electronic pipette, on dispense mode. Screw the caps back on each bottle a quarter turn, and incubate 30 minutes with stirring at 60±2° C.
9. Remove the caps and dispense 1.4 mL 1.0 N HCl into bottles, via repeater pipette, while stirring. Adjust pH to 4.0-4.7 using 0.5 N NaOH/HCl or 1.0 N NaOH/HCl. Conservatively rinse the pH probe with 50-60° C. nanopure water into the corresponding 500PCB.
10. Add 150 μL amyloglucosidase solution to each 500PCB via electronic pipette, on dispense mode, while stirring. Screw the caps back on each bottle a quarter turn, and incubate for 30 minutes with stirring at 60±2° C.
11. Remove rack containing 500PCBs from 60±2° C. bath. Place entire rack in boiling bath (97.5±2.5° C.). Incubate for 20 minutes. The purpose of this step is to denature all of the enzymes and stop any further digestion.
12. Remove rack containing 500PCBs from the boiling bath. CAUTION: Be sure to wear proper PPE while removing rack from boiling bath.
13. Allow samples to cool for at least 10 minutes on the benchtop.
14. Remove polygon stir bars from each bottle and rinse with nanopure water back into the corresponding 500PCB. Bring the mass of each 500PCB to the bottle tare weight plus 30±0.1 g using nanopure water.
15. Add 180 mL of pre-chilled (approximately −20° C.) anhydrous reagent alcohol to each bottle. Add o-rings to caps. Be sure to mix the combined solution well by agitation/swirling of solution while cap is on bottle.
16. Loosen caps and place in explosion proof −20±5° C. freezer for at least 3 hours. Loose caps are necessary so that pressure can equilibrate with temperature.
17. Balance all 500PCBs with corresponding caps and o-rings in pairs to ±0.5 g of each other using anhydrous reagent alcohol.
18. Place balanced 500PCBs in a rack and into 60±2° C. bath for EXACTLY 5 minutes to temper the solution. Remove entire rack from bath, quickly dry the outside of each bottle, and proceed immediately to centrifugation.
19. Place the 500PCBs in the tempered JA-10 rotor with each balanced pair on the opposite sides of the rotor, symmetrically directly across from one another. Flush the drum with nitrogen for 5 minutes. Centrifuge according to established parameters.
20. Carefully remove the first 500PCB from rotor. Use the aspirator to transfer the supernatant from the 500PCB to the aspirator receptacle. Flush the aspirator tube using a conservative amount of anhydrous reagent alcohol. Be careful not to aspirate pellet particles. Once the aspiration is complete, remove the o-ring from the cap. If RO is to be analyzed from sample, place "wide tube" aspirator stopper on top of round bottom flask for RO roto-evaporator.
21. Screw the cap back onto the 500PCB, and set the bottle aside. Repeat steps 20-21 for each individual sample.
In the event pellet particles are accidently transferred to the RO roto-evaporator flask, do the following:
   i. Aspirate from RO roto-evaporator flask containing particles to a clean RO roto-evaporator flask.
   ii. Use the de-fatting solvent in step 22(b) below to quantitatively transfer particles in the original RO roto-evaporator flask to the corresponding 500PCB containing the TDF pellet.
22. De-fatting of TDF Pellet:
   a. Add a polygon stir bar to each 500PCB.
   b. Add approximately 10 mL of 2:1 (v/v) Acetone/Methanol (de-fatting solvent) to each 500PCB.
   c. Using a rubber policeman, scrape down any residue remaining on the sides of the 500PCB into the de-fatting solvent.
   d. Rinse the rubber policeman and the sides of the 500PCB into the 500PCB using approximately 20 additional mLs of de-fatting solvent.
   e. Screw the cap back on each 500PCB a quarter turn, and place into rack.
   f. Incubate at 60±2° C. for 30 min with constant stirring.
   g. Remove from water bath.
   h. Start a timer for 10 minutes.
     i. During the 10 minute cool down at room temperature, remove and rinse stir bars back into 500PCB with de-fatting solvent.
     ii. Add o-rings to caps.
     iii. Bring total weight of 500PCB with cap and o-ring to approximately 97 g with de-fatting solvent to ensure bottle is at proper volume for safe centrifugation.
     iv. Balance 500PCB pairs (±0.5 g) with caps and o-rings using de-fatting solvent.
23. Place the 500PCBs in the tempered JA-10 rotor with each balanced pair on the opposite sides of the rotor, directly across from one another. Flush the drum with nitrogen for 5 minutes. Centrifuge according to established parameters.
24. Place waste container in the "narrow tube" aspirator jar.
25. Carefully remove the first 500PCB from rotor, and use the aspirator to remove the supernatant from the 500PCB. Once supernatant has been removed, flush the aspirator tube with a conservative amount of nanopure water. Place cap, with o-ring, back on bottle immediately. Repeat this step for each sample. Be careful not to transfer pellet particles.

26. Place each 500PCB containing the TDF pellet in the Shell-Freezer at −75° C. to −90° C. Incubate for at least 10 minutes.
27. Remove 500PCBs from Shell-Freezer. Wipe off excess ethanol. Quickly place each 500PCB with corresponding cap, in a 1200 mL Freeze-Dryer flask with adapter and apply vacuum.
28. Allow to dry for 16 hours minimum on Freeze Dryer. Ensure that a blank is always included with each freeze dryer batch.
29. Remove the first Freeze-Dryer flask from the Freeze-Dryer. Weigh back each individual 500PCB, without cap to four decimal places.
30. Transfer the TDF pellet in each 500PCB to a labeled storage tube and homogenize. Repeat steps 29-30 for each 1200 mL Freeze-Dryer flask.
31. Using the residue weights, determine ash and protein content by:

| Residue Weight Range (g) | Protocol |
| --- | --- |
| ≤0.00050 | Report Result < 0.1% |
| 0.00051-0.00600 | SDS Preparation |
|  | SDS Ash |
|  | SDS Protein |
| >0.00601 | Direct Ash |
|  | Direct Protein |

NOTE:
If unable to get a full 0.00601 g of residue out of the 500PCB, LOW RESIDUE WEIGHT METHOD FOR PREPARING PROTEIN AND ASH SAMPLES can be followed.

Samples Containing Inulin
1. After pH adjusting the sample, add 150 μL amyloglucosidase solution to each 50PCT or 500PCB via electronic pipette, on dispense mode, while stirring. Start the timer for 20 minutes.
   a. For each individual sample run in 50PCTs, screw the cap back on the tube, vortex until all sample is suspended, and resume incubation with stirring at 60±2° C. Make sure all caps are loose when placed into 60±2° C. bath after vortexing.
   b. For each sample run in 500PCB, screw the caps back on each bottle a quarter turn.
2. Remove the caps and add 0.5 mL fructozyme (≥200 U/mL) via repeater pipette to bottles while stirring. Start the timer for 30 minutes.
   a. For each individual sample run in 50PCTs, screw the cap back on the tube, vortex until all sample is suspended, and resume incubation with stirring at 60±2° C. Make sure all caps are loose when placed into 60±2° C. bath after vortexing.
   b. For each sample run in 500PCB, screw the caps back on each bottle a quarter turn.
3. Continue with digestion from procedure.

De-Fatting (Option 1 and 2)
Option 1—Bulk Centrifuge De-Fatting
1. Weigh a clean 500 mL centrifuge bottle without cap and record actual weight to four decimal places (Bottle).
2. Weigh 5±0.5 g of sample into the centrifuge bottle and record the actual weight to four decimal places (Sample Weight).
3. Add 300 mL of 2:1 (v/v) Acetone/Methanol (de-fatting solvent) to the sample.
4. Add a polygon stir bar to the centrifuge bottle.
5. Screw on the cap (without o-ring) a quarter turn. The cap must be left loose on the bottle threads so that pressure can equalize with temperature treatment.
6. Incubate at 60±2° C. for 30 minutes with constant stirring.
7. Remove the centrifuge bottles from the 60±2° C., then remove the stir bars and rinse any solids off the stir bars with de-fatting solvent.
8. Cool for 10 minutes to room temperature.
9. Add an o-ring to the cap of the centrifuge bottle.
10. Weigh the bottle with cap and make equal to another sample or blank by weight within 0.5 g by adding de-fatting solvent to either bottle of the pair as necessary.
11. Place the pair of balanced centrifuge bottles directly opposite (symmetrically) from each other in the tempered JA-10 rotor.
12. Flush the centrifuge drum with nitrogen for 5 minutes. Centrifuge according to established parameters.
13. Aspirate off the supernatant de-fatting solvent from the pellet and discard appropriately.
14. Place in the shell freezer −75° C. to −90° C. for at least 10 minutes.
15. Remove the cap, and add to a 1200 mL Freeze-Dryer flask. Freeze dry for at least 16 hours.
16. Determine the Net weight of the bottle without cap and o-ring for the dried, de-fatted sample (De-fatted Sample+Bottle).
17. Determine De-fat Recovery by calculation below.
Option 1 Calculation:

Recover=[(De-fatted Sample+Bottle)−(Bottle)]/Sample Weight

Where,
De-fatted Sample+Bottle=the weight of the de-fatted sample plus the centrifuge bottle (step 16);
Bottle=the tare weight of the centrifuge bottle (step 1); and
Sample Weight=the weight of the sample prior to de-fatting (step 2)
   NOTE: Recovery is always less than 1. Whenever possible, check de-fat recovery against Fat and Moisture labs results for the sample to verify complete fat extraction.

Option 2—Ankom, Soxhlet and Manual De-fatting
Accepted Equipment:
1. Ankom Fat Extractor XT20 or XT15.
2. Soxhlet extractions using petroleum ether and Alundum extraction thimbles may also be used (extract for a minimum of 4 hours).
3. Manual extraction using petroleum ether and Alundum thimbles or Whatman #1 filter paper lining a Whatman single thickness extraction thimble may also be used. Extract for a minimum of 4 hours.

Ankom Fat Extractor
Part A: Sample Weigh Up
1. Label filter bags with sample ID and de-fat bag number using a solvent-proof black marker. Place the bag on the balance and tare the balance (set to zero). Remove the bag and record the positive tare weight to the nearest 0.0001 g (BW).
2. Weigh sample into the bag. Seal the top of the bag (the heat sealer should be set at approximately 6). Place the bag back on the balance and record the exact weight of the sample to the nearest 0.0001 g (SW). Repeat this procedure for each of the samples. A maximum of 20 bags can be run at one time.
3. Dry the samples in a drying oven (safety or explosion-proof type) at 100-125° C. for a minimum of 3 hours.

Part B: Fat Extraction
Equipment. Ankom Fat Extractor XT20

1. Turn on fume hood above Fat Extractor XT20, compressed Nitrogen cylinder, and chiller associated with Fat Extractor XT20.
2. Place the filter bags into the Fat Extractor XT20. Select Program F1. Set the temperature to 90° C. and the time to 60 minutes.
3. Press "Auto Start" to start the run. When the run has been completed, remove the samples from the rack and place in the 105±5° C. oven for a minimum of 1 hour.
4. Remove samples from oven and place in desiccators. Allow the samples to cool to room temperature.
5. Re-weigh as soon as possible after cooling. Record the weight to the nearest 0.0001 g (FW).
6. Inspect the particle size of recovered solids. If solids do not pass through a 16-mesh screen, grind in a Magic Bullet.

Equipment. Ankom Fat Extractor XT15
1. Turn on fume hood above Fat Extractor XT15 and chiller associated with Fat Extractor XT15.
2. Check solvent level at sight glass on front of instrument.
3. Place the filter bags into the Fat Extractor XT15 and press Enter. Select time 60 minutes. Select heat temperature 90° C.
4. Press "Start" to start the run. When the run has been completed, remove the samples from the rack and place in the 105±5° C. oven for a minimum of 1 hour.
5. Remove samples from oven and place in desiccator. Allow the samples to cool to room temperature.
6. Re-weigh as soon as possible after cooling. Record the weight to the nearest 0.0001 g (FW).
7. Inspect the particle size of recovered solids. If solids do not pass through a 16-mesh screen, grind in a Magic Bullet.

Part C: Fat Extraction Calculation $$\text{RECOVERY} = \frac{(FW - BW)}{SW}$$

Where:
BW=tare weight in grams of the filter bag
FW=final weight in grams of the bag after extraction and drying
SW=sample weight in grams
NOTE: Recovery is always less than 1

Special Calculations for Low-Recovery Samples:
In the case of high fat and/or high fat/moisture samples, the residue from the extraction process may not be adequate to run a sample. In the event that 0.5 g cannot be recovered from the extraction, calculate recovery as above combining the weights from all bags.
If 0.01>RECOVERY>0.001, then report % Fiber as not detected to the following limit:
% Fiber <1%
If RECOVERY <0.001, then report % Fiber as not detected to the following limit:
% Fiber <0.1%

Low Residue Weight Method for Preparing Protein and Ash Samples
1. Add 1.00 mL (1000 uL) of 1% SDS to the dried sample in the 500PCB using an electronic pipette.
NOTE: Alternative volumes of 1% SDS may be used for solubilization and for measurements of protein and ash if special circumstances should call for it. Alternative volumes and weights should be recorded as they are used in the final calculation.
2. Using a plastic spatula, loosen all pellet residue from the sides of the 500PCB so that it is suspended in the added 1% SDS.
3. Use a transfer pipette to scrape any particles off of the plastic spatula and rinse back into 500PCB.
4. Sonicate the bottle in a 40±3° C. sonicator water bath for 5 minutes to solubilize residue.
5. Use a transfer pipette to transfer as much as possible the volume of SDS plus sample residue into a labeled tube. Ensure that as much residue as possible comes out of the transfer pipette with the SDS.
6. Using a prepared large orifice pipette tip with an electronic pipette on mix/dispense mode, mix the SDS solution from the labeled tube 3 times, or enough times to get an even suspension, at max speed.
7. While solution is evenly suspended, quickly pipet 250 μL (or half of the recovered solution from the centrifuge bottle if less than 1 mL was recovered) into a tared crucible for ash measurement; a tared capsule for protein measurement by Dumas; or a tared candy cup for protein measurement by Kjeldahl. Tare weights should all be recorded to five decimal places. Weigh the crucible, capsule or cup with the added suspension and record the weight to five decimal places.
8. Prepare blanks in triplicate for ash, protein by Dumas, or protein by Kjeldahl respectively by pipetting 250 uL of the stock 1% SDS solution (or half of the recovered solution from the centrifuge bottle if less than 1 mL was recovered) into a tared crucible for ash measurement; a tared capsule for protein measurement by Dumas; or a tared candy cup for protein measurement by Kjeldahl. Tare weights should all be recorded to five decimal places. Weigh the crucible, capsule or cup with the stock 1% SDS solution and record the weight to five decimal places.
9. Proceed to measure ash by ASH FOR RESIDUES PREPARED BY SDS SOLUTION.
10. Proceed to measure protein by Kjeldahl or Dumas combustion by PROTEIN FOR RESIDUES PREPARED BY SDS SOLUTION.

Ash for Residues Prepared by SDS Solution
1. Determine a tare weight to five decimal places for a clean, dry, pre-ashed 5 mL crucible.
2. Transfer approximately 250 uL of the 1% SDS sample described in step 7 of LOW RESIDUE WEIGHT METHOD FOR PREPARING PROTEIN AND ASH SAMPLES (or half of the recovered solution from the centrifuge bottle if less than 1 mL was recovered) to the crucible and record the weight of the residue suspension to 5-decimal places.
3. Dry the 1% SDS residue suspension and the stock 1% SDS blank solutions in a 105±5° C. forced air oven until visually dry (approximately 45 min).
4. Place the crucibles in an ash oven set to 580° C. for at least 3 hours.
5. Remove crucibles from ash oven and place in a desiccator until crucibles reach room temperature (at least 2 hours).
6. Weigh back crucibles and record weights to five decimal places.

Protein for Residues Prepared by SDS Solution
for Measurement of Protein by Dumas Combustion—
1. Transfer approximately 250 μL of the 1% SDS sample described in step 7 of LOW RESIDUE WEIGHT METHOD FOR PREPARING PROTEIN AND ASH SAMPLES (or half of the recovered solution from the centrifuge bottle if less than 1 mL was recovered) to the capsule and record the weight of the residue suspension to five decimal places.
2. Dry the 1% SDS residue suspension and the stock 1% SDS blank solutions in a 105±5° C. forced air oven until visually dry (approximately 45 min).
3. Measure total protein in capsules.
For Measurement of Protein by Kjeldahl.

1. Measure total protein in samples from step 7 of LOW RESIDUE WEIGHT METHOD FOR PREPARING PROTEIN AND ASH SAMPLES.

Measurement of Ash by Direct Weighing of Fiber Residue

1. Determine a tare weight to 5-decimal places for a clean, dry, pre-ashed 1.3 or 5 mL crucible ($W_t$).
2. Depending on total quantity of residue recovered, weigh between 3-15 mg of fiber residue into the crucible and record the weight to five decimal places ($W_r$). Be sure that enough fiber residue remains to use for protein determination.
3. Place the crucibles in an ash oven set to 580° C. for at least 3 hours.
4. Remove crucibles from ash oven and place in a desiccator until crucibles reach room temperature (approximately 2 hours)
5. Weigh back crucibles and record weights to five decimal places ($W_a$).

Measurement of Protein by Direct Weighing of Fiber Residue

1. Weigh between 3-15 mg of fiber residue into a Dumas foil if measuring protein by Combustion or a Kjeldahl candy cup if measuring protein by Kjeldahl. Record the sample weight to five decimal places.
2. Determine the protein content.

Calculations:

Unless otherwise indicated, all parts and percentages are by weight and all molecular weights are weight average molecular weights. The foregoing detailed description has been given for clarity of understanding only. No unnecessary limitations are to be understood therefrom.

The following examples may provide additional details about dietary fiber determination in accordance with this disclosure.

Example 1

Fat Removal Efficacy from Insoluble Dietary Fiber

A 0.5 gram sample of Oat flour ground to homogeneity to pass a 0.5 mm screen but retained by a 0.3 mm screen was dispersed in 20 mL of 50 mM MES-Tris buffer, pH 8.2. The dispersed sample was digested with a heat-stable bacterial alpha-amylase at 95-100 C for 25 minutes, digested with bacterial Subtilisin A protease for 30 minutes at 60 C, pH adjusted to 4.5 and digested with fungal amyloglucosidase for 30 minutes as prescribed by AOAC official method 991.43. The sample was tempered and centrifuged in a Beckman-Coulter J26-XPI using a JA 30.50Ti rotor at 26,000 rpm (81,800×g) for 30 minutes at 15 C to pellet the insoluble dietary fiber. The supernatant containing the soluble dietary % Ash in Residue
$$A = \frac{(W_a - W_t) \times 100}{W_r}$$

Where:
$W_a$ = Weight of crucible after ashing
$W_t$ = Tare weight of crucible
$W_r$ = Residue weight Blank
$$\text{Blank} = \frac{(100 - P_b - A_b) \times R_b}{100}$$

Where:
$P_b$ = % protein of the blank
$A_b$ = % ash of the blank
$R_b$ = Residue weight of the blank % Insoluble Dietary Fiber
$$IDF = \frac{(((100 - P_i - A_i) \times R_i)/100) - B_i}{W} \times 100\%$$

Where:
$P_i$ = % protein of insoluble portion
$A_i$ = % ash of insoluble portion
$R_i$ = Residue weight of insoluble portion
$B_i$ = Blank of insoluble portions
W = Sample weight % Soluble Dietary Fiber
$$SDF = \frac{(((100 - P_s - A_s) \times R_s)/100) - B_s}{W} \times 100\%$$

Where:
$P_s$ = % protein of soluble portion
$A_s$ = % ash of soluble portion
$R_s$ = Residue weight of soluble portion
$B_s$ = Blank of soluble portion
W = Sample weight % Total Dietary Fiber
$$TDF = \frac{(((100 - P - A) \times R)/100) - B}{W} \times 100\%$$

Where:
P = % protein of sample
A = % ash of sample
R = Residue weight of sample
B = Blank
W = Sample weight % Dietary Fiber for De-fat Samples =
DF × De-fat Recovery Where:
DF = % IDF, SDF or TDF LOW RESIDUE WEIGHT METHOD
% Residue Ash (RA)
RA = ((Sa − Ba) × (Vr + Rw))/Rw Where:
Sa = Solution Ash Result (%)
Ba = 1% SDS Blank Ash (%)
Vr = Volume of 1% SDS added to Residue (mL)
Rw = Residue Weight (g)

LOW RESIDUE WEIGHT METHOD
% Residue Protein (RP)
RP = ((Sp − Bp) × (Vr + Rw))/Rw Where:
Sp = Solution Protein (%)
Bp = 1% SDS Blank Protein (%)
Vr = Volume of 1% SDS added to Residue (mL)
Rw = Residue Weight (g)

and dissoluted digestate of non-dietary fiber components was removed from the insoluble dietary fiber pellet by aspiration. The remaining insoluble dietary fiber pellet was then treated by various conditions as described in the tables to remove residual fat from the insoluble dietary fiber pellet. Residual fat in the insoluble dietary fiber pellet was measured following freeze-drying of the pellet and then either gravimetrically determining the residue remaining in the organic solvent used to extract the insoluble fiber or direct determination of fatty acid residues by gas chromatography using AOAC 996.06. The most effective fat removal method found for isolated insoluble dietary fiber was to break up the pellet using 30 mL 2:1 Acetone/Methanol, then to stir for 30 minutes in a 60 C water bath and centrifuged in a Beckman-Coulter J26-XPI using a JA 30.50Ti rotor at 26,000 rpm (81,800×g) for 30 minutes at 25 C. The results are provided in the following tables:

| Pre-Centrifugation Defat Conditions for Tested for Insoluble Fiber | | | | | | | | | | | |
|---|---|---|---|---|---|---|---|---|---|---|---|
| Experiment | Primary Solvent | Volume (mL) | Additional Solvent | Solvent Addition Temp (° C.) | Primary Agitation | Primary Agitation Time (min) | Primary Agitation Temp (° C.) | Secondary Agitation | Secondary Agitation Time (min) | Secondary Agitation Temp (° C.) |
| 1 | Acetone | 20 | None | 25 | Pipet suction | 5 | 25 | None | None | None |
| 2 | Acetone | 10 | None | 25 | Pipet suction | 5 | 25 | None | None | None |
| 3 | Acetone | 20 | None | 25 | Vortex | 5 | 25 | None | None | None |
| 4 | Acetone | 20 | None | 25 | Vortex | 5 | 25 | None | None | None |
| 5 | Acetone | 20 | None | 25 | Vortex | 5 | 25 | None | None | None |
| 6 | Petroleum Ether | 20 | None | 25 | Vortex | 5 | 25 | None | None | None |
| 7 | 2:1 Chloroform/MeOH | 20 | None | 25 | Vortex | 5 | 25 | None | None | None |
| 8 | Acetone | 30 | None | 25 | Vortex | 10 | 25 | Orbital Shaker, 150 RPM | 10 | 30 |
| 9 | 2:1 Chloroform/MeOH | 30 | None | 25 | Vortex | 10 | 25 | Orbital Shaker, 150 RPM | 10 | 30 |
| 10 | 2:1 Acetone/MeOH/0.5% Hac | 30 | None | 25 | Vortex | 10 | 25 | Orbital Shaker, 150 RPM | 10 | 30 |
| 11 | 2:1 Acetone/MeOH | 30 | None | 25 | Vortex | 10 | 25 | Orbital Shaker, 150 RPM, plus Vortex | 10 | 30 |
| 12 | 2:1 Acetone/MeOH | 30 | None | 25 | Vortex | 10 | 25 | No Agitation | 10 | 25 |
| 13 | 2:1 Acetone/MeOH | 30 | None | 25 | Vortex | 10 | 25 | Orbital Shaker, 150 RPM, plus Vortex | 10 | 30 |
| 14 | 2:1 Acetone/MeOH | 30 | None | 25 | Vortex | 5 | 25 | Water Bath plus Vortex | 5 | 60 |
| 15 | 2:1 Acetone/MeOH | 30 | None | 25 | Vortex | 5 | 25 | Orbital Shaker, 150 RPM, plus Vortex | 15 | 25 |
| 16 | 2:1 Acetone/MeOH | 30 | None | 25 | Vortex | 5 | 25 | Water Bath | 10 | 60 |
| 17 | 2:1 Acetone/MeOH | 30 | None | 25 | Vortex | 5 | 25 | Water Bath | 20 | 60 |
| 18 | 2:1 Acetone/MeOH | 30 | None | 25 | Vortex | 5 | 25 | Water Bath | 20 | 60 |
| 19 | 2:1 Acetone/MeOH | 30 | None | 25 | Vortex | 5 | 25 | Water Bath | 20 | 60 |
| 20 | 2:1 Acetone/MeOH | 30 | Water Pretreatment 1 mL, 10 min | 100 | Vortex | 5 | 25 | Water Bath | 30 | 60 |
| 21 | 2:1 Acetone/MeOH | 30 | Water Pretreatment 1 mL, 10 min | 100 | Vortex | 5 | 25 | Orbital Shaker, 350 RPM | 30 | 60 |
| 22 | 2:1 Acetone/MeOH | 30 | Water Pretreatment 5 mL, 10 min | 100 | Vortex | 5 | 25 | Water Bath | 30 | 60 |
| 23 | 2:1 Acetone/MeOH | 30 | Water Pretreatment 5 mL, 10 min | 100 | Vortex | 5 | 25 | Orbital Shaker, 350 RPM | 30 | 60 |
| 24 | 2:1 Acetone/MeOH | 30 | None | 25 | Vortex | 5 | 25 | Orbital Shaker, 350 RPM | 30 | 60 |
| 25 | 2:1 Acetone/MeOH | 30 | None | 25 | Vortex | 5 | 25 | Water Bath/Stir Plate-Bars | 30 | 60 |

| Centrifugation Defat Conditions for Tested for Insoluble Fiber | | | | | | | | | |
|---|---|---|---|---|---|---|---|---|---|
| Experiment | Secondary Agitation | Secondary Agitation Time (min) | Secondary Agitation Temp (° C.) | RPM | RCF (xg) | Spin Time (min) | Rotor Temp (° C.) | Residual Fat (%) | Fat Analysis Method | Pellet Integrity (High, Medium, Low) |
| 1 | None | None | None | 10,000 | 18,000 | 10 | 4 | 25 | Evaporation Residue | Low |

-continued

| | | | | | | | | | | | |
|---|---|---|---|---|---|---|---|---|---|---|---|
| 2 | None | None | None | 10,000 | 18,000 | 10 | 4 | 15 | Evaporation Residue | Low |
| 3 | None | None | None | 18,185 | 60,000 | 30 | 4 | ND | ND | Low |
| 4 | None | None | None | 18,185 | 40,000 | 10 | 4 | ND | ND | Low |
| 5 | None | None | None | 22,272 | 60,000 | 15 | 8 | ND | ND | Low |
| 6 | None | None | None | 26,000 | 81,800 | 15 | 25 | ND | ND | Medium |
| 7 | None | None | None | 26,000 | 81,800 | 15 | 25 | ND | ND | Medium |
| 8 | Orbital Shaker, 150 RPM | 10 | 30 | 26,000 | 81,800 | 30 | 25 | ND | ND | Low |
| 9 | Orbital Shaker, 150 RPM | 10 | 30 | 26,000 | 81,800 | 30 | 25 | >25 | Evaporation Residue | Medium |
| 10 | Orbital Shaker, 150 RPM | 10 | 30 | 26,000 | 81,800 | 30 | 25 | ~5 | Evaporation Residue | Medium |
| 11 | Orbital Shaker, 150 RPM, plus Vortex | 10 | 30 | 26,000 | 81,800 | 30 | 25 | ~5 | Evaporation Residue | Medium |
| 12 | No Agitation | 10 | 25 | 26,000 | 81,800 | 30 | 25 | ~5 | Evaporation Residue | Medium |
| 13 | Orbital Shaker, 150 RPM, plus Vortex | 10 | 30 | 26,000 | 81,800 | 30 | 25 | ~5 | Evaporation Residue | Medium |
| 14 | Water Bath plus Vortex | 5 | 60 | 26,000 | 81,800 | 30 | 25 | ~5 | Evaporation Residue | Medium |
| 15 | Orbital Shaker, 150 RPM, plus Vortex | 15 | 25 | 26,000 | 81,800 | 30 | 25 | 5 | Evaporation Residue | Medium |
| 16 | Water Bath | 10 | 60 | 26,000 | 81,800 | 30 | 25 | ~5 | Evaporation Residue | Medium |
| 17 | Water Bath | 20 | 60 | 26,000 | 81,800 | 30 | 25 | ~5 | Evaporation Residue | Medium |
| 18 | Water Bath | 20 | 60 | 26,000 | 81,800 | 30 | 25 | ~5 | Evaporation Residue | Medium |
| 19 | Water Bath | 20 | 60 | 26,000 | 81,800 | 30 | 25 | 1.38 | AOAC 996.06 | Medium |
| 20 | Water Bath | 30 | 60 | 26,000 | 81,800 | 30 | 25 | ~5 | Evaporation Residue | Low |
| 21 | Orbital Shaker, 350 RPM | 30 | 60 | 26,000 | 81,800 | 30 | 25 | ~5 | Evaporation Residue | Low |
| 22 | Water Bath | 30 | 60 | 26,000 | 81,800 | 30 | 25 | ~5 | Evaporation Residue | Low |
| 23 | Orbital Shaker, 350 RPM | 30 | 60 | 26,000 | 81,800 | 30 | 25 | ~5 | Evaporation Residue | Low |
| 24 | Orbital Shaker, 350 RPM | 30 | 60 | 26,000 | 81,800 | 30 | 25 | 0.85 | AOAC 996.06 | Medium |
| 25 | Water Bath/Stir Plate-Bars | 30 | 60 | 26,000 | 81,800 | 30 | 25 | 0.82 | AOAC 996.06 | High |

Example 2

Thermal Gradient Conditions for Improved Pelleting During Centrifugation

A 0.5 gram sample of Oat flour ground to homogeneity to pass a 0.5 mm screen but retained by a 0.3 mm screen was dispersed in 20 mL of 50 mM MES-Tris buffer, pH 8.2. The dispersed sample was digested with a heat-stable bacterial alpha-amylase at 95-100 C for 25 minutes, digested with bacterial Subtilisin A protease for 30 minutes at 60 C, pH adjusted to 4.5 and digested with fungal amyloglucosidase for 30 minutes as prescribed by AOAC official method 991.43. Insoluble dietary fiber was treated as described in the table to determine the optimal tempering conditions which yield the pellet of greatest integrity following centrifugation in a Beckman-Coulter J26-XPI using a JA 30.50Ti rotor at 26,000 rpm (81,800×g) for 30 minutes at 15 C to pellet the insoluble dietary fiber. For total dietary fiber, the sample following digest was precipitated with a final concentration of 85% alcohol for 3 hours at −20 C, tempered as described in the table, and centrifuged at 10,000 rpm (17,700×g) using a Beckman-Coulter J26-XPI with a JA-10 rotor at 4 C for 30 minutes for evaluation of pellet integrity. Optimal tempering conditions for pelleting insoluble were found to be a 10 minute incubation at 60 C prior to centrifugation. For total dietary fiber, incubation at 60 C for 5 minutes prior to centrifugation gave best results. The results are provided in the following table:

| | | | First Pre-Spin Incubation | First Incubation | Second Pre-Spin Incubation | Second Incubation | Centrifugation | | | | Pellet Integrity (High, |
|---|---|---|---|---|---|---|---|---|---|---|---|
| Fiber Type | Buffer | Volume (mL) | Temperature (° C.) | Time (min) | Temperature (° C.) | Time (min) | RPM | RCF (xg) | Spin Time (min) | Rotor Temp (° C.) | Medium, Low) |
| Insoluble | 50 mM MES-Tris, pH 8.2 | 20 | −80 | 5 | NA | NA | 21,000 | 41,000 | 30 | 4 | Low |

| Tempering Conditions for Improved Pelleting of Insoluble and Total Dietary Fiber | | | | | | | | | | | |
|---|---|---|---|---|---|---|---|---|---|---|---|
| Fiber Type | Buffer | Volume (mL) | First Pre-Spin Incubation Temperature (° C.) | First Incubation Time (min) | Second Pre-Spin Incubation Temperature (° C.) | Second Incubation Time (min) | Centrifugation | | | | Pellet Integrity (High, Medium, Low) |
| | | | | | | | RPM | RCF (xg) | Spin Time (min) | Rotor Temp (° C.) | |
| Insoluble | 50 mM MES-Tris, pH 8.2 | 20 | −80 | 5 | NA | NA | 17,000 | 39,000 | 20 | 4 | Low |
| Insoluble | 50 mM MES-Tris, pH 8.2 | 20 | −80 | 5 | NA | NA | 17,000 | 39,000 | 30 | 4 | Low |
| Insoluble | 50 mM MES-Tris, pH 8.2 | 20 | ~30-34 | 10 | NA | NA | 26,000 | 81,800 | 15 | 15 | Medium |
| Insoluble | 50 mM MES-Tris, pH 8.2 | 20 | 25 | ~120 | NA | NA | 26,000 | 81,800 | 30 | 15 | Medium |
| Insoluble | 50 mM MES-Tris, pH 8.2 | 20 | 30 | 10 | NA | NA | 26,000 | 81,800 | 15 | 15 | Low |
| Insoluble | 50 mM MES-Tris, pH 8.2 | 20 | −80 | 5 | NA | NA | 26,000 | 81,800 | 30 | 15 | Medium |
| Insoluble | 50 mM MES-Tris, pH 8.2 | 20 | 25 | 80 | −80 | 5 | 26,000 | 81,800 | 30 | 15 | High |
| Insoluble | 50 mM MES-Tris, pH 8.2 | 20 | 25 | 60 | −80 | 5 | 26,000 | 81,800 | 30 | 15 | Medium |
| Insoluble | 50 mM MES-Tris, pH 8.2 | 20 | 60 | 60 | −80 | 5 | 26,000 | 81,800 | 30 | 15 | Medium |
| Insoluble | 50 mM MES-Tris, pH 8.2 | 20 | 60 | 10 | −80 | 5 | 26,000 | 81,800 | 30 | 15 | Medium |
| Insoluble | 50 mM MES-Tris, pH 8.2 | 20 | 60 | 10 | NA | NA | 26,000 | 81,800 | 30 | 15 | High |
| Total | 50 mM MES-Tris, pH 8.2 | 20 | 20 | 65 | NA | NA | 10,000 | 17,700 | 30 | 4 | Medium |
| Total | 50 mM MES-Tris, pH 8.2 | 20 | −20 | 0 | NA | NA | 10,000 | 17,700 | 30 | 4 | Low |
| Total | 50 mM MES-Tris, pH 8.2 | 20 | 40 | 10 | NA | NA | 10,000 | 17,700 | 30 | 4 | High |
| Total | 50 mM MES-Tris, pH 8.2 | 20 | 60 | 5 | NA | NA | 10,000 | 17,700 | 30 | 4 | High |

Example 3

Comparison of Dietary Fiber Recovery Using Centrifugation Versus Filtration (Group 1)

Twelve 0.5 gram samples of different U.S. manufactured food products which had been ground to homogeneity to pass a 0.5 mm screen but retained by a 0.3 mm screen were dispersed in 20 mL of 50 mM MES-Tris buffer, pH 8.2. The dispersed samples were digested with a heat-stable bacterial alpha-amylase at 95-100 C for 25 minutes, digested with bacterial Subtilisin A protease for 30 minutes at 60 C, pH adjusted to 4.5 and digested with fungal amyloglucosidase for 30 minutes as prescribed by AOAC official method 991.43. Half of the samples were filtered through a celite-containing crucible to separate insoluble and soluble dietary fiber and treated as prescribed in AOAC 991.43. The second half of the samples were tempered and centrifuged in a Beckman-Coulter J26-XPI using a JA 30.50Ti rotor at 26,000 rpm (81,800×g) for 30 minutes at 15 C to pellet the insoluble dietary fiber. The supernatant containing the soluble dietary and dissoluted digestate of non-dietary fiber components was removed from the insoluble dietary fiber pellet by aspiration. Insoluble dietary fiber isolated by centrifugation was de-fatted with 2:1 Acetone/Methanol, re-centrifuged, and dried with a freeze dryer. The quantity of dried insoluble dietary fiber was determined gravimetrically following blank subtraction and subtraction of determined total ash and protein. Soluble fiber in the isolated supernatant removed from the insoluble pellet was determined following precipitation with a final concentration of 85% alcohol for 3 hours at −20 C, tempered, and centrifuged at 10,000 rpm (17,700×g) using a Beckman-Coulter J26-XPI with a JA-10 rotor at 4 C for 30 minutes. The soluble fiber was freeze dried, de-fatted and the quantity of dried total dietary fiber was determined gravimetrically following blank subtraction and subtraction of determined total ash and protein. For total dietary fiber, the sample following digest was precipitated with a final concentration of 85% alcohol for 3 hours at −20 C and either treated as prescribed in AOAC991.43 using filtration or tempered, and centrifuged at 10,000 rpm (17,700×g) using a Beckman-Coulter J26-XPI with a JA-10 rotor at 4 C for 30 minutes. Supernatant was removed by aspiration and the total dietary fiber pellet was de-fatted with 2:1 Acetone/Methanol, re-centrifuged at 10,000 rpm (17,700×g) using a Beckman-Coulter J26-XPI with a JA-10 rotor at 4 C for 30 minutes. Following removal of the de-fatting solvent by aspiration, the sample was freeze dried. The quantity of dried total dietary fiber was determined gravimetrically following blank subtraction and subtraction of determined total ash and protein. Results comparing the total dietary fiber obtained using filtration by AOAC 991.43 or centrifugation are shown in the table. A significant increase in total dietary fiber yield using centrifugation was observed for all tested matrices. The results are provided in the following table:

| Recovery of Total Dietary Fiber by Centrifugation versus Filtration for U.S. Food Products | | | | | | | |
|---|---|---|---|---|---|---|---|
| | Filtration | | | Centrifugation | | | Relative |
| Matrix | Insoluble Fiber (g/100 g) | Soluble Fiber (g/100 g) | Total Fiber (g/100 g) | Insoluble Fiber (g/100 g) | Soluble Fiber (g/100 g) | Total Fiber (g/100 g) | Increase in Total Fiber Recovery (%) |
| Oat Flour | 6.1 | 4.1 | 10.2 | 6.0 | 5.6 | 11.6 | 13.5 |
| Oat-based RTE Cereal | 5.5 | 4.1 | 9.6 | 5.5 | 5.4 | 10.9 | 13.5 |
| Oat & Honey-based RTE Cereal | 4.0 | 3.0 | 7.0 | 4.4 | 4.2 | 8.6 | 22.9 |
| Multigrain-based RTE Cereal | 7.0 | 1.9 | 8.9 | 7.7 | 3.1 | 10.8 | 21.3 |
| Corn-based RTE Cereal | 8.3 | 0.5 | 8.8 | 8.7 | 1.2 | 9.9 | 12.5 |
| Wheat-based RTE Cereal | 8.5 | 2.1 | 10.7 | 9.4 | 3.3 | 12.7 | 18.7 |
| Rice-based RTE Cereal | 1.7 | 0.6 | 2.3 | 2.1 | 1.0 | 3.1 | 34.8 |
| Psyllium-based drink mix | 15.5 | 3.7 | 19.2 | 18.3 | 5.2 | 23.5 | 22.4 |
| Strawberry Yogurt | 0.2 | 0.5 | 0.7 | 0.1 | 0.9 | 1.0 | 42.9 |
| High-Fiber Peanut Bar | 11.7 | 1.4 | 13.1 | 12.4 | 1.6 | 14.0 | 6.9 |
| High-Fiber Soup | 1.2 | 1.0 | 2.2 | 1.6 | 1.1 | 2.7 | 22.7 |
| High-Fiber RTE Cereal | 15.3 | 1.3 | 16.6 | 16.0 | 1.7 | 17.7 | 6.6 |

Example 4

Comparison of Dietary Fiber Recovery Using Centrifugation Versus Filtration (Group 2)

Twelve 0.5 gram samples of different internationally manufactured food products which had been ground to homogeneity to pass a 0.5 mm screen but retained by a 0.3 mm screen were dispersed in 20 mL of 50 mM MES-Tris buffer, pH 8.2. The dispersed samples were digested with a heat-stable bacterial alpha-amylase at 95-100 C for 25 minutes, digested with bacterial Subtilisin A protease for 30 minutes at 60 C, pH adjusted to 4.5 and digested with fungal amyloglucosidase for 30 minutes as prescribed by AOAC official method 991.43. Half of the samples were filtered through a celite-containing crucible to separate insoluble and soluble dietary fiber and treated as prescribed in AOAC 991.43. The second half of the samples were tempered and centrifuged in a Beckman-Coulter J26-XPI using a JA 30.50Ti rotor at 26,000 rpm (81,800×g) for 30 minutes at 15 C to pellet the insoluble dietary fiber. The supernatant containing the soluble dietary and dissolved digestate of non-dietary fiber components was removed from the insoluble dietary fiber pellet by aspiration. Insoluble dietary fiber isolated by centrifugation was de-fatted with 2:1 Acetone/Methanol, re-centrifuged, and dried with a freeze dryer. The quantity of dried insoluble dietary fiber was determined gravimetrically following blank subtraction and subtraction of determined total ash and protein. Soluble fiber in the isolated supernatant removed from the insoluble pellet was determined following precipitation with a final concentration of 85% alcohol for 3 hours at −20 C, tempered, and centrifuged at 10,000 rpm (17,700×g) using a Beckman-Coulter J26-XPI with a JA-10 rotor at 4 C for 30 minutes. The soluble fiber was freeze dried, de-fatted and the quantity of dried total dietary fiber was determined gravimetrically following blank subtraction and subtraction of determined total ash and protein. For total dietary fiber, the sample following digest was precipitated with a final concentration of 85% alcohol for 3 hours at −20 C and either treated as prescribed in AOAC991.43 using filtration or tempered, and centrifuged at 10,000 rpm (17,700×g) using a Beckman-Coulter J26-XPI with a JA-10 rotor at 4 C for 30 minutes. Supernatant was removed by aspiration and the total dietary fiber pellet was de-fatted with 2:1 Acetone/Methanol, re-centrifuged at 10,000 rpm (17,700×g) using a Beckman-Coulter J26-XPI with a JA-10 rotor at 4 C for 30 minutes. Following removal of the de-fatting solvent by aspiration, the sample was freeze dried. The quantity of dried total dietary fiber was determined gravimetrically following blank subtraction and subtraction of determined total ash and protein. Results comparing the total dietary fiber obtained using filtration by AOAC 991.43 or centrifugation are shown in the table. A significant increase in total dietary fiber yield using centrifugation was observed for all tested matrices. The results are provided in the following table:

| Recovery of Total Dietary Fiber by Centrifugation versus Filtration for International Food Products | | | | | | | | |
|---|---|---|---|---|---|---|---|---|
| | | Filtration | | | Centrifugation | | | Relative |
| Matrix | Country | Insoluble Fiber (g/100 g) | Soluble Fiber (g/100 g) | Total Fiber (g/100 g) | Insoluble Fiber (g/100 g) | Soluble Fiber (g/100 g) | Total Fiber (g/100 g) | Increase in Total Fiber Recovery (%) |
| Wheat Flake RTE Cereal | Chile | | | 10.0 | | | 11.3 | 13.0 |
| Wheat Flake Chocolate RTE Cereal | France | 4.4 | 1.1 | 5.5 | 4.9 | 1.3 | 6.2 | 12.7 |
| Wheat Flake Yoghurt RTE Cereal | France | 3.9 | 1.0 | 4.9 | 4.9 | 2.0 | 6.9 | 40.8 |
| Wheat Flake & Fruits RTE Cereal | Mexico | | | 9.0 | | | 10.2 | 13.3 |
| Oat-based & Honey RTE Cereal | Mexico | | | 5.4 | | | 5.7 | 5.6 |
| Wheat Flake RTE Cereal | Poland | | | 5.9 | | | 6.9 | 16.9 |
| Wheat Flake, Chocolate&Orange Bar | Poland | | | 4.1 | | | 6.6 | 61.0 |
| Wheat Flake Milk Chocolate Bar | Poland | | | 7.6 | | | 10.7 | 40.8 |
| Wheat Flake Strawberry Bar | Poland | | | 4.7 | | | 7.1 | 51.1 |
| Wheat Flake & Fruits RTE Cereal | Poland | | | 5.7 | | | 8.7 | 52.6 |
| Chocolate RTE Cereal | Poland | | | 7.1 | | | 7.4 | 4.2 |
| Chocolate Grain Bars | Poland | | | 3.6 | | | 5.3 | 47.2 |

Recovery of Total Dietary Fiber by Centrifugation versus Filtration for International Food Products

| | | Filtration | | | Centrifugation | | | Relative |
|---|---|---|---|---|---|---|---|---|
| Matrix | Country | Insoluble Fiber (g/100 g) | Soluble Fiber (g/100 g) | Total Fiber (g/100 g) | Insoluble Fiber (g/100 g) | Soluble Fiber (g/100 g) | Total Fiber (g/100 g) | Increase in Total Fiber Recovery (%) |
| Wheat Flake & Fruits RTE Cereal | Russia | | | 6.5 | | | 9.0 | 38.5 |
| Wheat Flake Chocolate Bars | Switzerland | | | 4.8 | | | 8.4 | 33.3 |
| Oat-based & Honey RTE Cereal | United Kingdom | | | 6.1 | | | 8.5 | 39.3 |
| Multigrain-based RTE Cereal | United Kingdom | | | 7.1 | | | 10.1 | 42.3 |
| Oat-based RTE Cereal | United Kingdom | | | 8.2 | | | 8.6 | 4.9 |
| Wheat Flake & Cherry RTE Cereal | United Kingdom | | | 8.4 | | | 9.6 | 14.3 |

Example 5

Determination of Relationship Between Dumas Combustion and Kjeldahl

Figure 5:
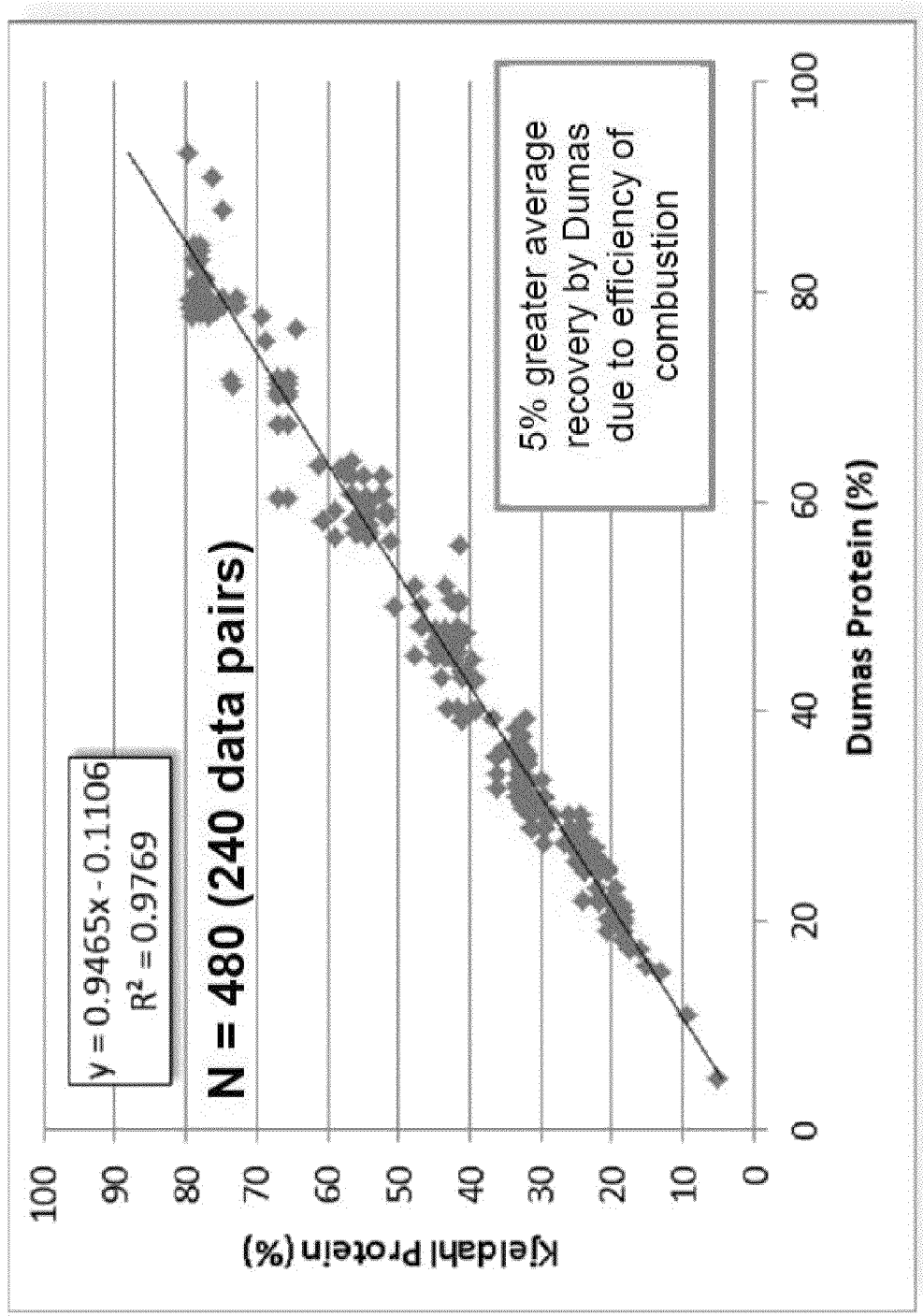
FIG. 5 illustrates an example relationship between Kjeldahl analysis and Dumas combustion for measuring protein content in a dietary fiber sample isolated by centrifuge separation.

Insoluble, soluble and total dietary fiber residues isolated by centrifuge from a variety of different matrices (e.g. cereal grains, soups, psyllium-containing beverages, chocolate, peanut butter, ready-to-eat cereal, and snack bars) were analyzed for total protein by both the Kjeldahl method and Dumas Combustion method. FIG. 5 illustrates the relationship determined between Kjeldahl analysis and Dumas combustion for the analyzed samples. A direct relationship between the two methods for all matrices and fiber types was observed by linear regression analysis of the data giving an r-square value of 0.977. The Kjeldahl protein result was lower than the Dumas Combustion protein result by approximately 5% as determined by the slope of the regression line (0.95). Based on this data, it was determined that using a nitrogen to protein conversion factor of 5.9 for Dumas Combustion can give the same protein result as Kjeldahl when a 6.25 nitrogen to protein conversion factor is used.

The invention claimed is:

1. A method comprising:
    a) enzymatically digesting a dietary fiber-containing sample and thereby producing a dietary fiber solution;
    b) centrifuging the dietary fiber solution so as to produce a pellet and a supernatant liquid;
    c) extracting the supernatant liquid from the pellet;
    d) combining the pellet with a solvent such that fat in the pellet dissolves in the solvent and thereby produces a dissolved fat solution;
    e) centrifuging the dissolved fat solution so as to produce a second pellet and a second supernatant liquid;
    f) drying the second pellet to produce a dried sample; and
    g) analyzing at least a portion of the dried sample to determine a content of non-dietary fiber components in the dried sample and determining therefrom a dietary fiber content in the dried sample.

2. The method of claim 1, further comprising adding alcohol to the dietary fiber solution prior to centrifuging the dietary fiber solution such that soluble dietary fiber is precipitated from the dietary fiber solution, wherein determining the dietary fiber content comprises determining a total dietary fiber content.

3. The method of claim 1, wherein analyzing at least a portion of the dried sample to determine the content of non-dietary fiber components in the dried sample comprises analyzing a first portion of the dried sample to determine a protein content and a second portion of the dried sample to determine an ash content.

4. The method of claim 3, wherein analyzing the first portion of the dried sample to determine the protein content comprises performing an analysis selected from the group consisting of a Dumas combustion analysis and a Kjeldahl digestion analysis on the first portion of the dried sample to determine a nitrogen content in the first portion of the dried sample.

5. The method of claim 1, wherein determining the dietary fiber content comprises determining the dietary fiber content based on gravimetric difference between a total weight of the dried sample and a weight of the non-dietary fiber components.

6. The method of claim 1, wherein determining the dietary fiber content comprises determining an insoluble dietary fiber content, and further comprising:
    adding alcohol to the supernatant liquid extracted from the pellet such that soluble dietary fiber is precipitated from the supernatant liquid;
    centrifuging the supernatant liquid with precipitated dietary fiber so as to produce a third pellet and a third supernatant liquid;
    extracting the third supernatant liquid from the third pellet;
    drying the third pellet to produce a second dried sample; and
    analyzing at least a portion of the second dried sample to determine a content of non-dietary fiber components in the second dried sample and determining therefrom a soluble dietary fiber content in the second dried sample.

7. The method of claim 6, further comprising de-fatting the third pellet prior to drying the third pellet.

8. The method of claim 6, wherein analyzing at least a portion of the second dried sample to determine the content of non-dietary fiber components in the second dried sample comprises analyzing a first portion of the second dried sample to determine a protein content and a second portion of the second dried sample to determine an ash content.

9. The method of claim 6, wherein determining the soluble dietary fiber content comprises determining the soluble dietary fiber content based on gravimetric difference between a total weight of the second dried sample and a weight of the non-dietary fiber components.

10. The method of claim 1, wherein
    a) enzymatically digesting the dietary fiber-containing sample comprises enzymatically digesting the dietary-fiber containing sample in a container configured to be inserted into a centrifuge,
    b) centrifuging the dietary fiber solution comprises centrifuging the container,
    c) extracting the supernatant liquid from the pellet comprises aspirating the supernatant liquid from the container while leaving the pellet in the container, d) combining the pellet with the solvent comprises adding the solvent to the container, and e) centrifuging the dissolved fat solution comprises centrifuging the container.

11. The method of claim 1, wherein centrifuging the dietary fiber solution comprises establishing a thermal gradient between the dietary fiber solution and centrifuge.

12. The method of claim 1, further comprising;

prior to enzymatically digesting the dietary fiber-containing sample, extracting the dietary fiber-containing sample from a food production line, and subsequent to analyzing at least a portion of the dried sample, adjusting an amount of dietary fiber added on the food production line based on the determined dietary fiber content.

* * * * *